United States Patent
Akiyama

(10) Patent No.: US 12,427,064 B2
(45) Date of Patent: Sep. 30, 2025

(54) PHOTOCOAGULATION APPARATUS, EYE FUNDUS OBSERVATION APPARATUS, METHOD OF CONTROLLING PHOTOCOAGULATION APPARATUS, METHOD OF CONTROLLING EYE FUNDUS OBSERVATION APPARATUS, AND RECORDING MEDIUM

(71) Applicant: Topcon Corporation, Tokyo (JP)

(72) Inventor: Hiroshi Akiyama, Souka (JP)

(73) Assignee: TOPCON CORPORATION, Tokyo (JP)

( * ) Notice: Subject to any disclaimer, the term of this patent is extended or adjusted under 35 U.S.C. 154(b) by 1152 days.

(21) Appl. No.: 17/257,864

(22) PCT Filed: Jun. 6, 2019

(86) PCT No.: PCT/JP2019/022572
§ 371 (c)(1),
(2) Date: Jan. 5, 2021

(87) PCT Pub. No.: WO2020/012840
PCT Pub. Date: Jan. 16, 2020

(65) Prior Publication Data
US 2021/0290437 A1    Sep. 23, 2021

(30) Foreign Application Priority Data
Jul. 11, 2018  (JP) .................. 2018-131236

(51) Int. Cl.
*A61F 9/008*    (2006.01)
*A61B 3/10*    (2006.01)
(Continued)

(52) U.S. Cl.
CPC .......... *A61F 9/00823* (2013.01); *A61B 3/102* (2013.01); *A61B 3/12* (2013.01);
(Continued)

(58) Field of Classification Search
CPC .......... A61B 3/102; A61B 3/12; A61B 3/135; A61B 3/14; A61F 9/00745; A61F 9/00821; A61F 2009/00851; A61F 2009/00863
See application file for complete search history.

(56) References Cited

U.S. PATENT DOCUMENTS 6,585,722 B1 * 7/2003 Abe .................. A61F 9/008
   606/4
RE46,493 E    8/2017 Lin
(Continued)

FOREIGN PATENT DOCUMENTS

EP    3533384 A1    9/2019
JP    2009-513279 A    4/2009
(Continued)

OTHER PUBLICATIONS

International Search Report and Written Opinion mailed on Jul. 23, 2019, received for PCT Application PCT/JP2019/022572, Filed on Jun. 6, 2019, 9 pages including English Translation.
(Continued)

*Primary Examiner* — Jennifer Pitrak McDonald
*Assistant Examiner* — Shreya Anjaria
(74) *Attorney, Agent, or Firm* — XSENSUS LLP

(57) ABSTRACT

A photocoagulation apparatus of some embodiment examples stores a first OCT image of a retina. The photocoagulation apparatus performs moving image photography of the retina to which aiming light is being applied, and repeatedly detects an aiming light image from a moving image. The photocoagulation apparatus moves a scan target area to include an aiming light application position. After treatment light application in response to user's instruction, the photocoagulation apparatus applies OCT scanning to the scan target area at a time of reception of the instruction, and constructs a second OCT image from acquired data. The
(Continued)

photocoagulation apparatus compares the first and second OCT images to acquire change information representing a tissue change caused by the treatment light, and displays a change image based on the change information together with a retinal image.

14 Claims, 16 Drawing Sheets

(51) Int. Cl.
    *A61B 3/12*     (2006.01)
    *A61B 3/135*     (2006.01)
    *A61B 3/14*     (2006.01)

(52) U.S. Cl.
    CPC ............... *A61B 3/135* (2013.01); *A61B 3/14* (2013.01); *A61F 2009/00851* (2013.01); *A61F 2009/00863* (2013.01)

(56) References Cited

U.S. PATENT DOCUMENTS

| | | |
|---|---|---|
| 2004/0039378 A1 | 2/2004 | Lin |
| 2006/0161145 A1 | 7/2006 | Lin et al. |
| 2006/0259022 A1 | 11/2006 | Lin |
| 2008/0259422 A1 | 10/2008 | Lin |
| 2008/0281306 A1 | 11/2008 | Lin |
| 2008/0300581 A1 | 12/2008 | Wiechmann et al. |
| 2012/0296320 A1 | 11/2012 | Lin et al. |
| 2014/0094784 A1* | 4/2014 | Charles ............... A61B 3/135 606/4 |
| 2014/0288537 A1 | 9/2014 | Wiechmann et al. |
| 2014/0324031 A1 | 10/2014 | Abe |
| 2015/0168127 A1 | 6/2015 | Takeno et al. |
| 2015/0223685 A1* | 8/2015 | Morishima ............... A61B 3/12 351/206 |
| 2015/0374228 A1 | 12/2015 | Satake et al. |
| 2016/0199227 A1* | 7/2016 | Luttrull ............... A61F 9/00823 606/4 |
| 2016/0256324 A1 | 9/2016 | Suzuki |
| 2016/0278983 A1* | 9/2016 | Claus ................. A61F 9/00821 |
| 2017/0042419 A1 | 2/2017 | Nakanishi et al. |
| 2017/0100285 A1* | 4/2017 | Hallen ............... A61B 5/14555 |
| 2017/0252213 A1* | 9/2017 | Furuuchi ............. A61F 9/00821 |
| 2017/0367889 A1* | 12/2017 | Swan ................. A61F 9/00821 |
| 2018/0055352 A1 | 3/2018 | Nakanishi et al. |
| 2018/0172426 A1 | 6/2018 | Takeno et al. |
| 2018/0360655 A1* | 12/2018 | Berlin ..................... A61B 3/13 |

FOREIGN PATENT DOCUMENTS

| | | |
|---|---|---|
| JP | 2009-516552 A | 4/2009 |
| JP | 2014-230743 A | 12/2014 |
| JP | 2015-131107 A | 7/2015 |
| JP | 2015-211734 A | 11/2015 |
| JP | 2016-10656 A | 1/2016 |
| JP | 2016-159070 A | 9/2016 |
| JP | 2016159068 A * | 9/2016 |
| JP | 2016-194459 A | 11/2016 |
| JP | 2016-206348 A | 12/2016 |
| JP | 2017-12431 A | 1/2017 |
| JP | 2017-153751 A | 9/2017 |
| JP | 2017-209385 A | 11/2017 |
| JP | 2018-68545 A | 5/2018 |
| JP | 2018-86272 A | 6/2018 |

OTHER PUBLICATIONS

Japanese Office Action issued Jun. 28, 2022, in corresponding Japanese Patent Application No. 2018-131236, 4 pp.

* cited by examiner

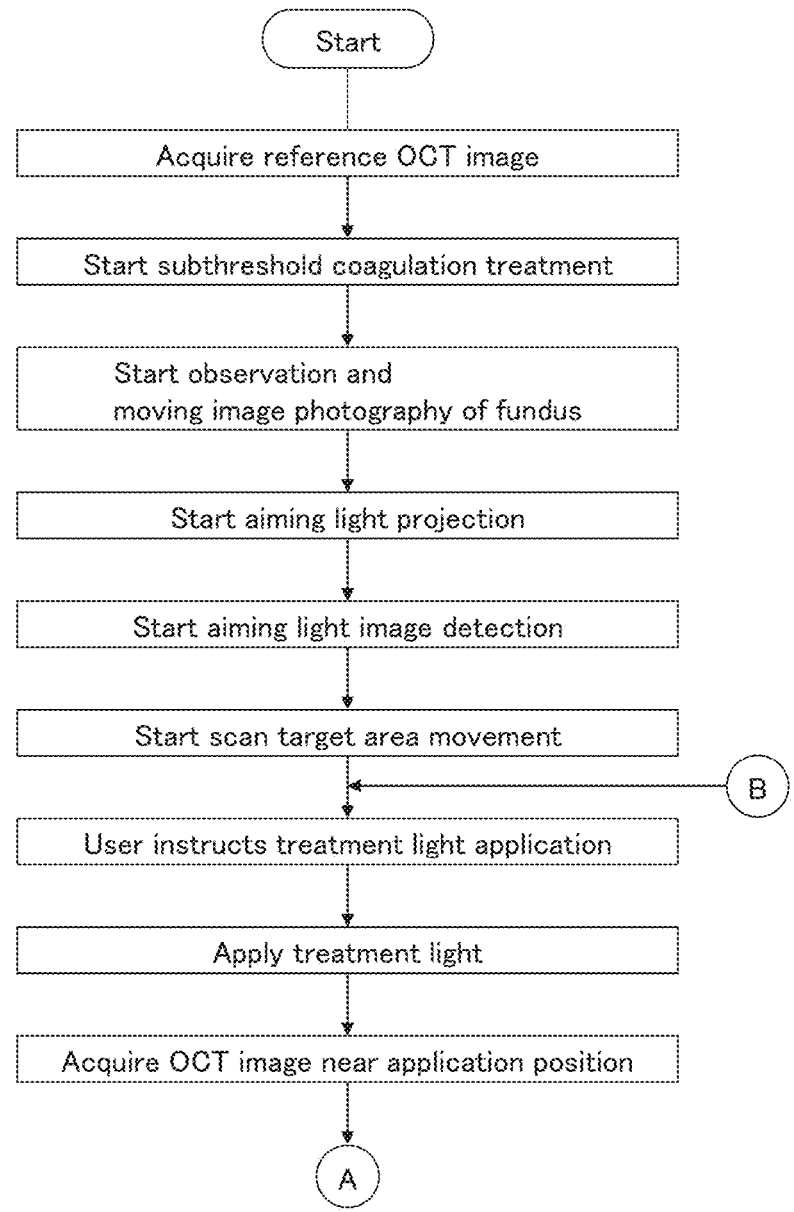

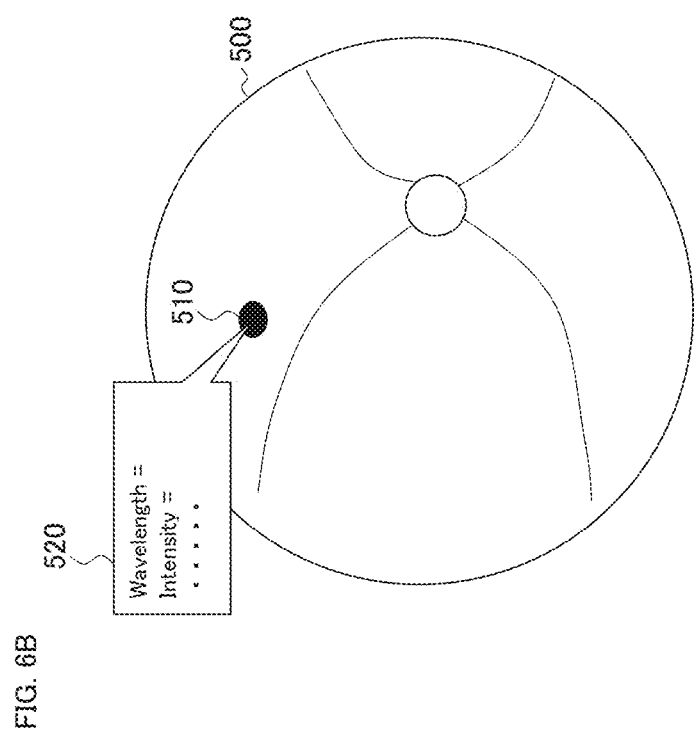

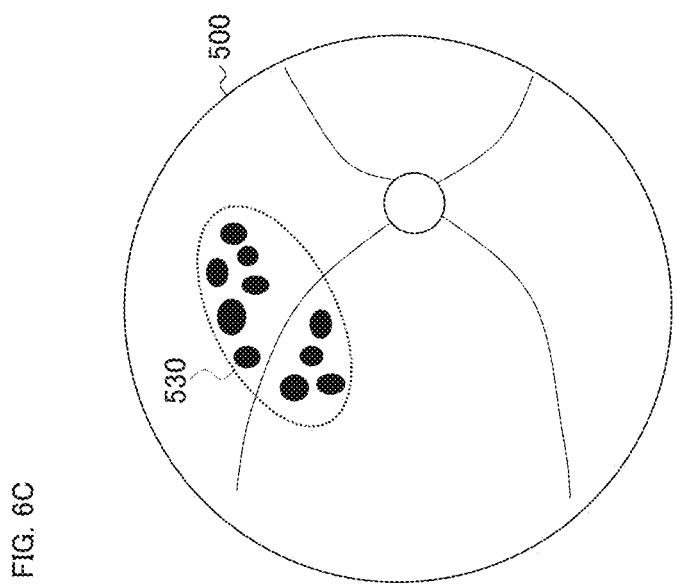

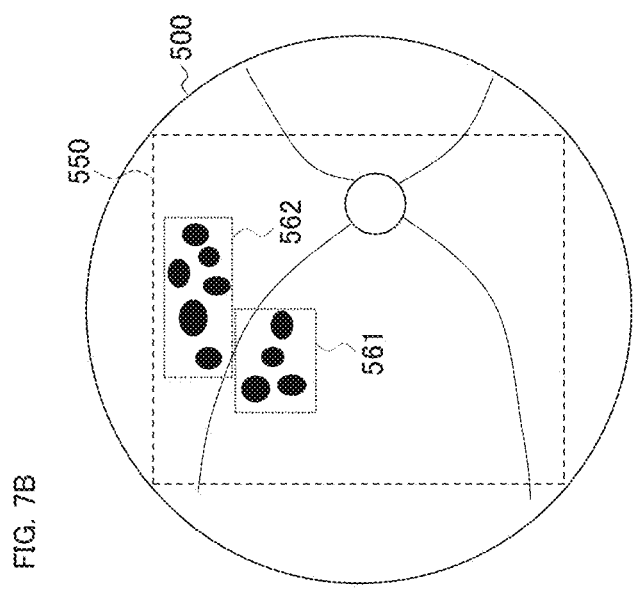

PHOTOCOAGULATION APPARATUS, EYE FUNDUS OBSERVATION APPARATUS, METHOD OF CONTROLLING PHOTOCOAGULATION APPARATUS, METHOD OF CONTROLLING EYE FUNDUS OBSERVATION APPARATUS, AND RECORDING MEDIUM

CROSS-REFERENCE TO RELATED APPLICATIONS

This application is a national stage (under 35 U.S.C. 371) of International Patent Application No. PCT/JP2019/022572, filed Jun. 6, 2019, claiming priority to Japanese Patent Application No. 2018-131236, filed Jul. 11, 2018, both of which are herein incorporated by reference in their entirety.

FIELD

The present disclosure relates to a photocoagulation apparatus, an eye fundus observation apparatus, a method of controlling a photocoagulation apparatus, a method of controlling an eye fundus observation apparatus, and a recording medium.

BACKGROUND

Photocoagulation is widely used in ophthalmic treatment. Photocoagulation is a treatment method or technique in which retinal tissue is coagulated by the heat generated by the absorption of laser light energy into the retinal pigment epithelium.

Photocoagulation is used for the following purposes, for example: for thermally destroying and adhering tissues in order to reinstate a detached retina to the retinal pigment epithelium; for thermally destroying an area around a retinal tear (break, hole) to prevent the retinal detachment from spreading so that the retinal tear do not deteriorate; and for burning (and sealing off) new blood vessels to stop or prevent bleeding of the eye fundus. In these applications, a target tissue is sufficiently cauterized and destroyed.

On the other hand, there is also a photocoagulation treatment method or technique that minimizes tissue cauterization. Such treatments are called subthreshold coagulation, micropulse subthreshold coagulation, selective pigment epithelial coagulation, or the like. Hereinafter, such a method or technique will be referred to as "subthreshold coagulation". Subthreshold coagulation is used, for example, for the following purposes: for destroying or damaging photoreceptor cells to reduce retinal metabolism in order to prevent the development of new blood vessels; and for destroying or damaging photoreceptor cells to reduce retinal metabolism in order to reduce diabetic macular edema.

Conventionally, photocoagulation has been performed while checking the degree of cauterization by observing a coagulation spot that appears on the surface of the retina. This conventional method or technique can be effective in photocoagulation for the purpose of sufficient cauterization of a tissue in which a cauterized area extends to the retinal surface. However, the conventional method or technique cannot be employed in subthreshold coagulation because no coagulation spot appears on the retinal surface in subthreshold coagulation.

Note that some techniques or technologies have also been developed to detect a tissue change that does not appear on the retinal surface (i.e., a tissue change in a deep part of the retina) using optical coherence tomography (OCT). However, it is still difficult to create a visualization of the state of a tissue change attributable to subthreshold coagulation in real time and to present the visualization to the user. In particular, it is extremely difficult to properly conduct subthreshold coagulation via a probe inserted into an eye.

BRIEF SUMMARY

An object of the present disclosure is to properly perform a visualization of a tissue change in a deep part of a retina that occurs in subthreshold coagulation.

The first aspect of some embodiment examples is a photocoagulation apparatus for applying subthreshold coagulation to a retina via a probe inserted into an eye. The photocoagulation apparatus includes: a light guiding system configured to guide aiming light and treatment light to the retina via the probe; a photography system configured to perform moving image photography of the retina at least while the light guiding system is guiding the aiming light; an image detecting processor configured to repeatedly detect an image of the aiming light from a moving image acquired by the moving image photography; an optical coherence tomography (OCT) system configured to apply an OCT scan to the retina; a movement controller configured to move a scan target area to include an application position of the aiming light on the retina by sequentially controlling the OCT system based on the image sequentially detected by the image detecting processor; a first memory configured to store a first OCT image of the retina in advance; a scan controller configured to control the OCT system, after the light guiding system guides the treatment light upon receiving an instruction from a user, to apply an OCT scan to the scan target area at a time of reception of the instruction; an image constructing processor configured to construct a second OCT image from data acquired by the OCT scan; a change information acquiring processor configured to acquire change information representing a tissue change in the retina caused by the treatment light by comparing the first OCT image and the second OCT image with each other; and a display controller configured to display a change image based on the change information on a display device together with a retinal image.

The second aspect of some embodiment examples is the photocoagulation apparatus of the first aspect, wherein the scan controller controls the OCT system to perform an OCT scan each time the light guiding system guides the treatment light, the image constructing processor constructs a second OCT image each time an OCT scan is performed by the OCT system, the change information acquiring processor acquires change information each time a second OCT image is constructed by the image constructing processor, and the display controller updates a display of a change image presented to the user together with the retinal image each time change information is acquired by the change information acquiring processor.

The third aspect of some embodiment examples is the photocoagulation apparatus of the second aspect, wherein the scan controller controls the OCT system to perform an OCT scan immediately after the light guiding system guides the treatment light.

The fourth aspect of some embodiment examples is the photocoagulation apparatus of any of the first to third aspects, wherein the scan controller controls the OCT system, after the treatment light is applied to each of a plurality of positions on the retina, to apply an OCT scan to an area that includes all of the plurality of positions, the image constructing processor constructs a third OCT image from data acquired by the OCT scan applied to the area, the change information acquiring processor acquires first change distribution information representing a distribution of tissue changes in the retina in the area by comparing the first OCT image and the third OCT image with each other, and the display controller controls the display device to display a first change distribution image based on the first change distribution information together with a retinal image.

The fifth aspect of some embodiment examples is the photocoagulation apparatus of the fourth aspect, wherein each of a plurality of scan target areas respectively corresponding to the plurality of positions is smaller than the area that includes all of the plurality of positions.

The sixth aspect of some embodiment examples is the photocoagulation apparatus of the fourth or fifth aspect, wherein the change information acquiring processor acquires second change distribution information representing a distribution of tissue changes in the retina in the area that includes all of the plurality of positions by comparing the second OCT image and the third OCT image with each other, and the display controller controls the display device to display a second change distribution image based on the second change distribution information together with a retinal image.

The seventh aspect of some embodiment examples is the photocoagulation apparatus of any of the first to sixth aspects, wherein the change information acquiring processor constructs motion contrast data from two or more OCT images acquired from substantially a same position of the retina at different times, and determines a tissue change in the retina from the motion contrast data.

The eighth aspect of some embodiment examples is the photocoagulation apparatus of any of the first to seventh aspects, wherein the display controller displays the retinal image on a first layer, and displays, on a second layer overlaid on the first layer, an image based on information acquired by the change information acquiring processor.

The ninth aspect of some embodiment examples is the photocoagulation apparatus of the eighth aspects, wherein the display controller displays an application condition of the treatment light guided by the light guiding system together with the image based on the information acquired by the change information acquiring processor.

The tenth aspect of some embodiment examples is the photocoagulation apparatus of any of the first to ninth aspects, further including: a second memory configured to store a template of a treatment report in advance; and a report creating processor configured to enter data in the template based at least on the information acquired by the change information acquiring processor.

The eleventh aspect of some embodiment examples is the photocoagulation apparatus of any of the first to tenth aspects, wherein the retinal image is any of an image of the retina acquired by a fundus camera, an image of the retina acquired by a scanning laser ophthalmoscope, an image of the retina acquired by a surgical microscope, an image of the retina acquired by a slit lamp microscope, and a front image of the retina acquired by using OCT.

The twelfth aspect of some embodiment examples is the photocoagulation apparatus of the first aspect, further including: an observation system configured for the user to observe a magnified image of the retina via an eyepiece; and an optical path coupling member configured to couple an optical path starting from the display device with an optical path of the observation system toward the eyepiece.

The thirteenth aspect of some embodiment examples is a photocoagulation apparatus for applying subthreshold coagulation to a retina, including: a light guiding system configured to guide aiming light and treatment light to the retina; a photography system configured to perform moving image photography of the retina at least while the light guiding system is guiding the aiming light; an image detecting processor configured to repeatedly detect an image of the aiming light from a moving image acquired by the moving image photography; an optical coherence tomography (OCT) system configured to apply an OCT scan to the retina; a movement controller configured to move a scan target area to include an application position of the aiming light on the retina by sequentially controlling the OCT system based on the image sequentially detected by the image detecting processor; a first memory configured to store a first OCT image of the retina in advance; a scan controller configured to control the OCT system, after the light guiding system guides the treatment light upon receiving an instruction from a user, to apply an OCT scan to the scan target area at a time of reception of the instruction; an image constructing processor configured to construct a second OCT image from data acquired by the OCT scan; a change information acquiring processor configured to acquire change information representing a tissue change in the retina caused by the treatment light by comparing the first OCT image and the second OCT image with each other; and a display controller configured to display a change image based on the change information on a display device together with a retinal image.

The fourteenth aspect of some embodiment examples is an eye fundus observation apparatus for applying subthreshold coagulation to a retina by a photocoagulation apparatus, including: a photography system configured to perform moving image photography of the retina at least while the photocoagulation apparatus is applying aiming light to the retina; an image detecting processor configured to repeatedly detect an image of the aiming light from a moving image acquired by the moving image photography; an optical coherence tomography (OCT) system configured to apply an OCT scan to the retina; a movement controller configured to move a scan target area to include an application position of the aiming light on the retina by sequentially controlling the OCT system based on the image sequentially detected by the image detecting processor; a first memory configured to store a first OCT image of the retina in advance; a scan controller configured to control the OCT system, after the photocoagulation apparatus applies treatment light upon receiving an instruction from a user, to apply an OCT scan to the scan target area at a time of reception of the instruction; an image constructing processor configured to construct a second OCT image from data acquired by the OCT scan; a change information acquiring processor configured to acquire change information representing a tissue change in the retina caused by the treatment light by comparing the first OCT image and the second OCT image with each other; and a display controller configured to display a change image based on the change information on a display device together with a retinal image.

The fifteenth aspect of some embodiment examples is a method of controlling a photocoagulation apparatus that applies subthreshold coagulation to a retina via a probe inserted into a patient's eye and includes a light guiding system configured to guide aiming light and treatment light to the retina via the probe and an optical coherence tomography (OCT) system configured to apply an OCT scan to the retina, the method including: a first memory step of storing a first OCT image of the retina; a photography step of performing moving image photography of the retina at least while the light guiding system is guiding the aiming light; an image detecting step of repeatedly detecting an image of the aiming light from a moving image acquired by the moving image photography; an OCT step of applying an OCT scan to the retina by the OCT system; a movement control step of moving a scan target area to include an application position of the aiming light on the retina by sequentially controlling the OCT system based on the image sequentially detected by the image detecting step; a scan control step of controlling the OCT system, after the light guiding system guides the treatment light upon receiving an instruction from a user, to apply an OCT scan to the scan target area at a time of reception of the instruction; an image constructing step of constructing a second OCT image from data acquired by the OCT scan; a change information acquiring step of acquiring change information representing a tissue change in the retina caused by the treatment light by comparing the first OCT image and the second OCT image with each other; and a display control step of displaying a change image based on the change information on a display device together with a retinal image.

The sixteenth aspect of some embodiment examples is a method of controlling a photocoagulation apparatus that applies subthreshold coagulation to a retina of a patient's eye and includes a light guiding system configured to guide aiming light and treatment light to the retina and an optical coherence tomography (OCT) system configured to apply an OCT scan to the retina, the method including: a first memory step of storing a first OCT image of the retina; a photography step of performing moving image photography of the retina at least while the light guiding system is guiding the aiming light; an image detecting step of repeatedly detecting an image of the aiming light from a moving image acquired by the moving image photography; an OCT step of applying an OCT scan to the retina by the OCT system; a movement control step of moving a scan target area to include an application position of the aiming light on the retina by sequentially controlling the OCT system based on the image sequentially detected by the image detecting step; a scan control step of controlling the OCT system, after the light guiding system guides the treatment light upon receiving an instruction from a user, to apply an OCT scan to the scan target area at a time of reception of the instruction; an image constructing step of constructing a second OCT image from data acquired by the OCT scan; a change information acquiring step of acquiring change information representing a tissue change in the retina caused by the treatment light by comparing the first OCT image and the second OCT image with each other; and a display control step of displaying a change image based on the change information on a display device together with a retinal image.

The seventeenth aspect of some embodiment examples is a method of controlling an eye fundus observation apparatus that is used for applying subthreshold coagulation to a retina of a patient's eye by a photocoagulation apparatus and includes an optical coherence tomography (OCT) system configured to apply an OCT scan to the retina, the method including: a first memory step of storing a first OCT image of the retina; a photography step of performing moving image photography of the retina at least while the photocoagulation apparatus is guiding aiming light; an image detecting step of repeatedly detecting an image of the aiming light from a moving image acquired by the moving image photography; an OCT step of applying an OCT scan to the retina by the OCT system; a movement control step of moving a scan target area to include an application position of the aiming light on the retina by sequentially controlling the OCT system based on the image sequentially detected by the image detecting step; a scan control step of controlling the OCT system, after the photocoagulation apparatus guides treatment light upon receiving an instruction from a user, to apply an OCT scan to the scan target area at a time of reception of the instruction; an image constructing step of constructing a second OCT image from data acquired by the OCT scan; a change information acquiring step of acquiring change information representing a tissue change in the retina caused by the treatment light by comparing the first OCT image and the second OCT image with each other; and a display control step of displaying a change image based on the change information on a display device together with a retinal image.

The eighteenth aspect of some embodiment examples is a program causing a computer to execute the method of any of the fifteenth, sixteenth, and seventeenth aspects.

The nineteenth aspect of some embodiment examples is a computer-readable non-transitory recording medium storing the program of the eighteenth aspect.

According to the embodiment example, a proper visualization of a tissue change in a deep part of a retina that occurs in subthreshold coagulation can be achieved.

BRIEF DESCRIPTION OF THE DRAWINGS

FIG. 4A is a flowchart illustrating a usage mode of the photocoagulation apparatus according to the embodiment example.

FIG. 6B is a schematic diagram for describing a usage mode of the photocoagulation apparatus according to the embodiment example.

FIG. 6C is a schematic diagram for describing a usage mode of the photocoagulation apparatus according to the embodiment example.

FIG. 7B is a schematic diagram for describing a usage mode of the photocoagulation apparatus according to the embodiment example.

DETAILED DESCRIPTION

Figure 1:
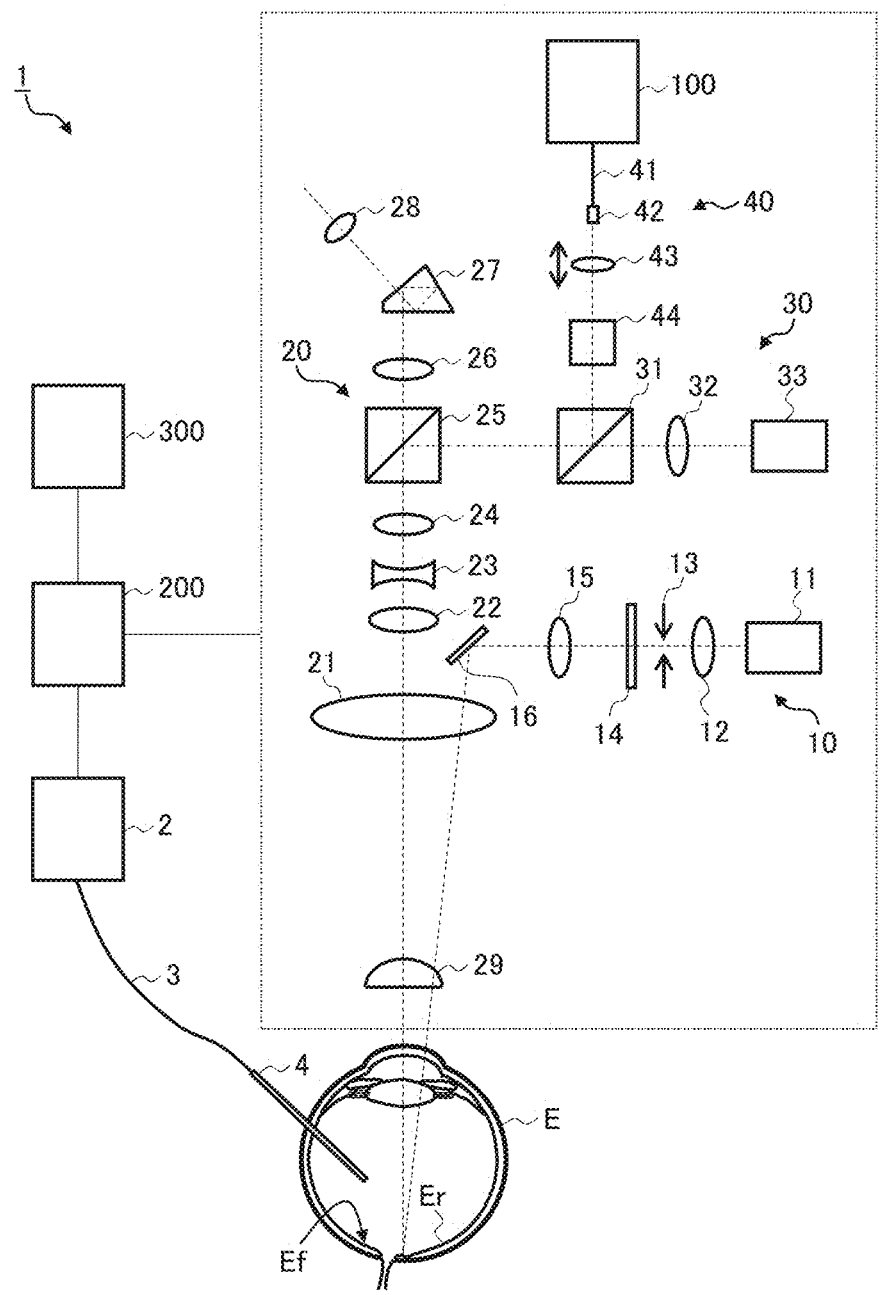
FIG. 1 is a schematic diagram illustrating the configuration of the photocoagulation apparatus according to the embodiment example.

The present disclosure provides descriptions of some embodiment examples of a photocoagulation apparatus, an eye fundus observation apparatus, a method of controlling a photocoagulation apparatus, a method of controlling an eye fundus observation apparatus, a program, and a recording medium with referring to the drawings. Any known techniques or technologies, including the items and matters disclosed in the documents cited herein, may be combined with the embodiment examples.

In the following disclosure, swept source OCT is employed as a method of optical coherence tomography (OCT). The method of OCT applicable to embodiment examples is not limited to swept source OCT, and may be spectral domain OCT, for example.

Swept source OCT is an imaging technique to construct an image performed by: splitting light emitted from a wavelength tunable light source into measurement light and reference light; superposing return light of the measurement light returning from the object with the reference light to generate interference light; detecting the interference light by a photodetector such as a balanced photodiode; and applying Fourier transform and other processes to the detection data acquired according to the wavelength sweeping and the measurement light scanning.

Spectral domain OCT is an imaging technique to construct an image performed by: splitting light from a low coherence light source into measurement light and reference light; superposing return light of the measurement light returning from the object with the reference light to generate interference light; detecting the spectral distribution of the interference light using a spectrometer; and applying Fourier transform and other processes to the spectral distribution detected.

As described above, swept source OCT is an OCT technique for acquiring a spectral distribution by time division, and spectral domain OCT is an OCT technique for acquiring a spectral distribution by space division. In addition, OCT techniques applicable to embodiment examples are not limited to these two, and may be any other morphological (structural) imaging OCT techniques such as time domain OCT or any functional imaging OCT techniques such as polarization OCT or blood flow measurement OCT.

In the present disclosure, "image data" and an "image" displayed based thereon may not be distinguished from one another unless otherwise mentioned. Likewise, a site or tissue of the patient's eye and an image representing the site or the tissue may not be distinguished from one another unless otherwise mentioned.

<Configuration of Photocoagulation Apparatus>

FIG. 1 shows the configuration of the photocoagulation apparatus according to the present embodiment example. In general, the photocoagulation apparatus includes a configuration for applying laser light for photocoagulation (subthreshold coagulation) to the retina, and a configuration for observing a magnified image of the eye fundus. The configuration for applying laser light to the retina may be the same as conventional configurations. For example, the configuration disclosed in Japanese Unexamined Patent Application Publication No. 2016-159070 or any modification thereof may be applied to the present embodiment example.

In the present embodiment example, a microscope for ophthalmic surgery is employed for magnified observation of the eye fundus. As an example of such a microscope for ophthalmic surgery, the one disclosed in Japanese Unexamined Patent Application Publication No. 2016-206348 is known. On the other hand, an ophthalmic microscope of any type such as a slit lamp microscope may be used for magnified observation of the eye fundus.

The photocoagulation apparatus 1 shown in FIG. 1 includes the laser unit 2, the illumination system 10, the observation system 20, the photography system 30, the OCT system 40, and the computer 200. The display device 300 may be included in the photocoagulation apparatus 1 or may be a peripheral device connected to the photocoagulation apparatus 1 (the computer 200).

<Laser Unit 2>

The laser unit 2 generates light to be applied to the patient's eye E. For example, as with the embodiment example disclosed in Japanese Unexamined Patent Application Publication No. 2016-159070, the laser unit 2 includes an aiming light source and a treatment light source.

The aiming light source generates aiming light for aiming at a location where laser treatment (subthreshold coagulation) is to be applied. The aiming light contains, for example, one or both of a visible light component and an infrared light component, and at least contains a wavelength component included in a wavelength band that can be detected by the image sensor 33 described later. The aiming light contains, in the present embodiment example, at least a visible light component for observation through the observation system 20.

The treatment light source emits treatment laser light (treatment light). The treatment light may be visible laser light or invisible laser light depending on the intended use. In addition, the treatment light source may include a plurality of laser light sources or a single laser light source that emits laser light having different wavelengths.

The laser unit 2 includes a configuration for selectively outputting aiming light and treatment light. Further, in the case where two or more treatment light sources are provided, the laser unit 2 further includes a configuration for selectively outputting light from these treatment light sources.

The light output from the laser unit 2 is guided to the probe 4 through the optical fiber 3. The optical fiber 3 is connected to the base end of the probe 4. A part (including the tip) of the probe 4 is inserted into the patient's eye E through a hole formed in the sclera of the patient's eye E. The light guided to the probe 4 through the optical fiber 3 is emitted from the tip of the probe 4. Although not shown, other surgical instruments may be inserted into the eye.

<Illumination System 10>

The illumination system 10 projects illumination light onto the fundus Ef of the patient's eye E. The illumination system 10 includes the illumination light source 11, the condenser lens 12, the illumination field diaphragm 13, the slit plate 14, the collimator lens 15, and the reflector 16.

The illumination light source 11 outputs illumination light. The illumination light contains, for example, one or both of a visible light component and an infrared light component, and at least contains a wavelength component included in a wavelength band that can be detected by the image sensor 33 described later. Typically, illumination light containing only an infrared light component is employed in order to avoid miosis during fundus observation. The illumination light output from the illumination light source 11 is refracted by the condenser lens 12 and guided to the illumination field diaphragm 13.

The illumination field diaphragm 13 is an optical member that limits a region onto which the illumination light is projected. The illumination field diaphragm 13 is provided at a position optically conjugate with the front focal point of the objective lens 21. The illumination light that has passed through the illumination field diaphragm 13 is guided to the slit plate 14.

The slit plate 14 is a light shielding plate in which a plurality of light transmitting parts (slits) are formed. The shapes of the plurality of slits correspond to the shape of the reflecting surface of the reflector 16. The slit plate 14 is driven (moved) by a mechanism that is not shown in the drawings, and the plurality of slits are selectively placed in the optical path. The slit placed in the optical path is arranged at a position optically conjugate with the front focal point of the objective lens 21. The illumination light that has passed through the slit is guided to the collimator lens 15.

The collimator lens 15 converts the illumination light that has passed through the slit into a parallel light beam. The illumination light that has become a parallel light beam is reflected by the reflecting surface of the reflector 16 and is projected onto the patient's eye E via the objective lens 21 (and the front lens 29). The return light (reflected light) of the illumination light projected onto the patient's eye E enters the observation system 20.

<Observation System 20>

The observation system 20 provides a magnified image of the patient's eye E to the user (doctor) via the eyepiece 28. Similar to the embodiment example disclosed in Japanese Unexamined Patent Application Publication No. 2016-206348, the observation system 20 has a pair of left and right optical systems (not shown in the drawings). The optical system on the left side provides a magnified image to the user's left eye, and the optical system on the right side provides a magnified image to the right eye. As a result, the user is able to observe a magnified stereoscopic image of the patient's eye E. Below, unless otherwise mentioned, a description will be given of one of the left and right optical systems.

The observation system 20 includes the objective lens 21 common to the left and right optical systems. Further, each of the left and right optical systems includes the zoom lens groups 22, 23 and 24, the beam splitter 25, the imaging lens 26, the image uprighting prism (Dove prism) 27, and the eyepiece 28. Each of the left and right optical systems may include an eye width adjusting prism and/or a visual field diaphragm as in the embodiment example disclosed in Japanese Unexamined Patent Application Publication No. 2016-206348.

The return light of the illumination light projected onto the patient's eye E is guided by the objective lens 21 (via the front lens 29). The return light refracted by the objective lens 21 is guided to the zoom lens groups 22, 23 and 24.

The zoom lens groups 22, 23 and 24 are relatively moved in the direction along the optical axis by a mechanism that is not shown in the drawings. With such a configuration, the magnification for observation or photography of the patient's eye E can be changed. The return light refracted by the zoom lens groups 22, 23 and 24 is directed to the beam splitter 25.

The beam splitter 25 splits the optical path of the photography system 30 from the optical path of the observation system 20. In other words, the beam splitter 25 couples the optical path of the observation system 20 and the optical path of the photography system 30. With this, part of the return light incident on the beam splitter 25 via the zoom lens groups 22, 23 and 24 is guided to the imaging lens 26, and another part of the return light is guided to the photography system 30.

The return light guided to the imaging lens 26 is directed to the image uprighting prism 27 after being subjected to the refraction action of the imaging lens 26. The image uprighting prism 27 converts the image (inverted image) formed by the imaging lens 26 into an upright image. The user may observe the upright image through the eyepiece 28.

In the case where the eye width adjusting prism mentioned above is provided, the distance between the left and right optical systems can be adjusted in accordance with the eye width (the distance between the left eye and the right eye) of the user. In addition, the visual field diaphragm mentioned above acts to limit the visual field of the user.

The front lens 29 is inserted in a position between the front focal point of the objective lens 21 and the patient's eye E at the time of observation of the fundus. In the case of anterior eye segment observation, the front lens 29 is removed from the optical path. Similar to the embodiment example disclosed in Japanese Unexamined Patent Application Publication No. 2016-206348, a plurality of front lenses that has mutually different refractive powers (e.g., 40 diopters, 80 diopters, 120 diopters) is prepared, and these front lenses are selectively used.

While the present embodiment example employs a Galilean stereo microscope, a Greenough stereo microscope may also be employed. In a Galilean stereo microscope, the left and right optical systems are provided with a common objective lens and the left and right optical axes are arranged in parallel to each other. Meanwhile, the left and right optical systems are provided with separate objective lenses and the left and right optical axes are arranged in a non-parallel manner in a Greenough stereo microscope. An example of a Greenough stereo microscope employable in some embodiment examples can be found in the disclosure of Japanese Unexamined Patent Application Publication No. 2017-012431.

<Photography System 30>

The photography system 30 is capable of performing moving image photography of the retina Er of the patient's eye E. The photography system 30 includes the beam splitter 31, the imaging lens 32, and the image sensor 33. The image sensor 33 may be, for example, a charge-coupled device (CCD) image sensor or a complementary metal oxide semiconductor (CMOS) image sensor.

The return light guided to the optical path of the photography system 30 by the beam splitter 25 of the observation system 20 is directed to the beam splitter 31. The optical path of the OCT system 40 branches from the optical path of the photography system 30 via the beam splitter 31. In other words, the beam splitter 31 couples the optical path of the photography system 30 and the optical path of the OCT system 40 with each other. The beam splitter 31 is typically a dichroic mirror that reflects light of the wavelength band used in the OCT system 40 while transmitting light of the wavelength band used in the photography system 30.

The return light guided to the imaging lens 32 is directed to the image sensor 33 after being subjected to the refraction action of the imaging lens 32. The image sensor 33 is capable of performing moving image photography at a predetermined photographing rate (frame rate). The photographing rate may be fixed or variable.

<October System 40>

The OCT system 40 applies an OCT scan to the retina Er of the patient's eye E. The OCT system 40 includes the OCT unit 100, the optical fiber 41, the collimator lens unit 42, the OCT focusing lens 43, and the optical scanner 44.

Figure 2:
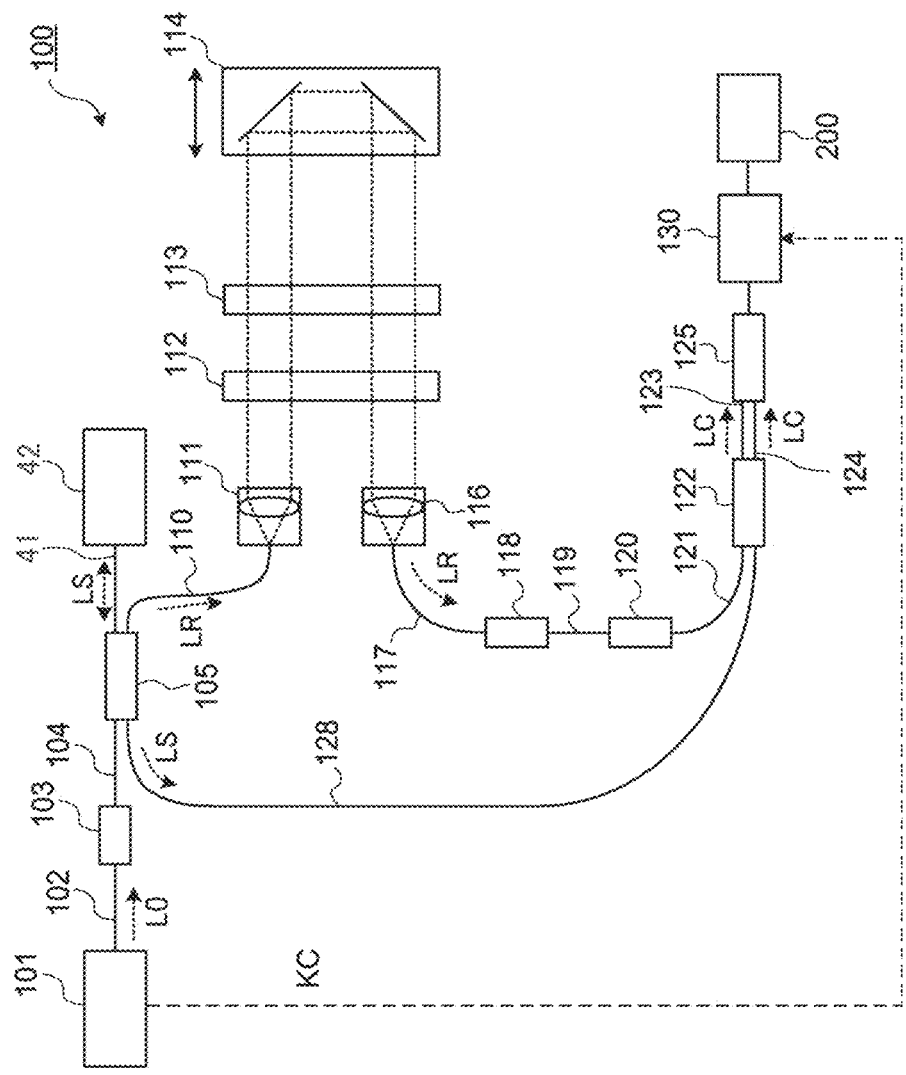
FIG. 2 is a schematic diagram illustrating the configuration of the photocoagulation apparatus according to the embodiment example.

The exemplary OCT unit 100 shown in FIG. 2 is provided with the optical system for performing swept source OCT. The optical system includes an interference optical system. The interference optical system is configured to split light emitted from a wavelength tunable light source into measurement light and reference light, superpose the return light of the measurement light projected onto the patient's eye E with the reference light having traveled through the reference optical path, thereby yielding interference light. Then, the interference optical system detects the interference light. The data (i.e., a detection signal, an interference signal) obtained by detecting the interference light is a signal representing the spectrum of the interference light and is sent to the computer 200.

The light source unit 101 includes, for example, a near-infrared wavelength tunable laser configured to vary wavelengths of emitted light at high speed. The low coherence light L0 output from the light source unit 101 is guided to the polarization device 103 through the optical fiber 102, and the polarization state of the light L0 is regulated. Further, the light L0 with regulated polarization state is guided to the fiber coupler 105 through the optical fiber 104 and is split into the measurement light LS and the reference light LR. The optical path of the measurement light LS is referred to as a measurement arm, and the optical path of the reference light LR is referred to as a reference arm.

The reference light LR generated by the fiber coupler 105 is guided through the optical fiber 110 to the collimator lens 111, is converted into a parallel light beam, travels through the optical path length correction member 112 and the dispersion compensation member 113, and is guided to the retroreflector 114. The optical path length correction member 112 acts to match the optical path length of the reference light LR and that of the measurement light LS with each other. The dispersion compensation member 113 acts to eliminate the difference between the dispersion characteristics of the reference light LR and that of the measurement light LS. The retroreflector 114 is movable along the optical path of the reference light LR incident on the retroreflector 114. With this, the length of the reference arm is changed. The change in the length of the reference arm may be utilized for operations such as optical path length correction according to axial length and interference condition adjustment.

After passing through the retroreflector 114, the reference light LR travels through the dispersion compensation member 113 and the optical path length correction member 112, is converted from a parallel light beam to a convergent light beam by the collimator lens 116, and is incident on the optical fiber 117. The reference light LR having entered the optical fiber 117 is guided to the polarization device 118, and the polarization state of the reference light LR is regulated. Then, the reference light LR is guided to the attenuator 120 through the optical fiber 119, and the light amount of the reference light LR is regulated. Subsequently, the reference light LR is guided to the fiber coupler 122 through the optical fiber 121.

Meanwhile, the measurement light LS generated by the fiber coupler 105 is guided to the collimator lens unit 42 through the optical fiber 41 and is converted to a parallel light beam. Then, the measurement light LS passes through the OCT focusing lens 43 and the optical scanner 44, and then is reflected by the beam splitter 31. Subsequently, the measurement light LS is reflected by the beam splitter 25 and is projected onto the patient's eye E via the zoom lens groups 24, 23, and 22, as well as the objective lens 21 (and further, the front lens 29).

The measurement light LS is reflected and scattered at various depths of the patient's eye E. The return light of the measurement light LS returning from the patient's eye E travels along the measurement arm in the opposite direction to the measurement light LS projected onto the patient's eye E, is directed to the fiber coupler 105, and then is directed to the fiber coupler 122 via the optical fiber 128.

The fiber coupler 122 superposes the measurement light LS incident through the optical fiber 128 with the reference light LR incident through the optical fiber 121, to generate interference light. The fiber coupler 122 splits the generated interference light at a predetermined splitting ratio (e.g., 1 to 1) to generate a pair of interference light LC. The pair of interference light LC is guided to the detector 125 through the optical fibers 123 and 124, respectively.

The detector 125 includes, for example, a balanced photo diode. The balanced photodiode includes a pair of photodetectors for respectively detecting the pair of the interference light LC. The balanced photodiode outputs a difference between a pair of detection signals corresponding to the pair of the interference light LC respectively obtained by the pair of photodetectors. The detector 125 sends the output (difference signal) to the data acquisition system (DAQ) 130.

The clock KC is supplied from the light source unit 101 to the data acquisition system 130. The clock KC is generated in the light source unit 101 in synchronization with the output timings of wavelengths varied over a predetermined wavelength range by the wavelength tunable type light source. For example, the light source unit 101 is configured to split the light L0 of each output wavelength to generate two pieces of split light, apply an optical delay to one of the two pieces of split light, combine the resulting two pieces of split light, detect the combined light, and generate the clock KC based on the detection signal of the combined light. The data acquisition system 130 performs sampling of the signal (difference signal) input from the detector 125 based on the clock KC. The data acquisition system 130 sends the data obtained by the sampling to the computer 200.

In general, an ophthalmic OCT apparatus is provided with an element for changing the difference between the measurement arm length and the reference arm length (i.e., optical path length difference) in order to move the coherence gate in the depth direction (axial direction). While an element for changing the reference arm length (the retroreflector 114 or a reference mirror) is provided in the present example, an element for changing the measurement arm length may be employed.

The OCT focusing lens 43 is moved in the direction along the measurement arm to conduct focus adjustment of the measurement arm (that is, to change the focal position of the measurement arm).

The optical scanner 44 is placed at a position substantially optically conjugate with respect to the pupil of the patient's eye E when the front lens 29 is inserted in the optical path.

The optical scanner 44 is configured to deflect the measurement light LS guided through the measurement arm. An example of the optical scanner 44 is provided by a galvano scanner configured to be capable of two dimensional scanning. Typically, the optical scanner 44 includes a one dimensional scanner for deflecting the measurement light LS in the first direction (+x and −x directions), and another one dimensional scanner for deflecting the measurement light LS in the second direction orthogonal to the first direction (+y and −y directions). The former may be referred to as an x-scanner and the latter as a y-scanner. When such a configuration is employed, for example, either one of the x-scanner and the y-scanner may be placed at the optically conjugate position described above. Alternatively, the optically conjugate positions may be placed at a location between the x-scanner and the y-scanner.

<Computer 200>

The computer 200 controls each part (each element) of the photocoagulation apparatus 1. Further, the computer 200 executes various kinds of data processing.

The computer 200 includes, for example, a processor, a random access memory (RAM), a read only memory (ROM), a hard disk drive, and a communication interface. A storage such as the hard disk drive stores various kinds of computer programs. The computer programs are executed by the processor of the computer 200. The computer 200 may include an operation device, an input device, a display device, etc.

Note that the "processor" as used in the present disclosure is hardware for executing a set of commands described in a software program. Such a processor typically includes an arithmetic unit, a resistor, a peripheral circuit, and the like. For example, the processor refers to a circuit or an electrical circuit configuration (or circuitry) such as a central processing unit (CPU), a graphics processing unit (GPU), a microprocessing unit (MPU), a digital signal processor (DSP), an application specific integrated circuit (ASIC), a programmable logic device (e.g., a simple programmable logic device (SPLD), a complex programmable logic device (CPLD), or a field programmable gate array (FPGA)), or the like. For example, the processor loads a program stored in storage hardware (e.g., a memory circuit or a storage), and executes the program, thereby implementing the functions according to a corresponding embodiment example. The processor may include at least part of the storage hardware.

The computer 200 may include a user interface (not shown in the drawings). The user interface includes a display part and an operation part. The display part may include the display device 300. The operation part includes various kinds of operation devices and input devices. The user interface may include a device having both the display function and the operation function, such as a touch panel display.

<Processing System>

Figure 3:
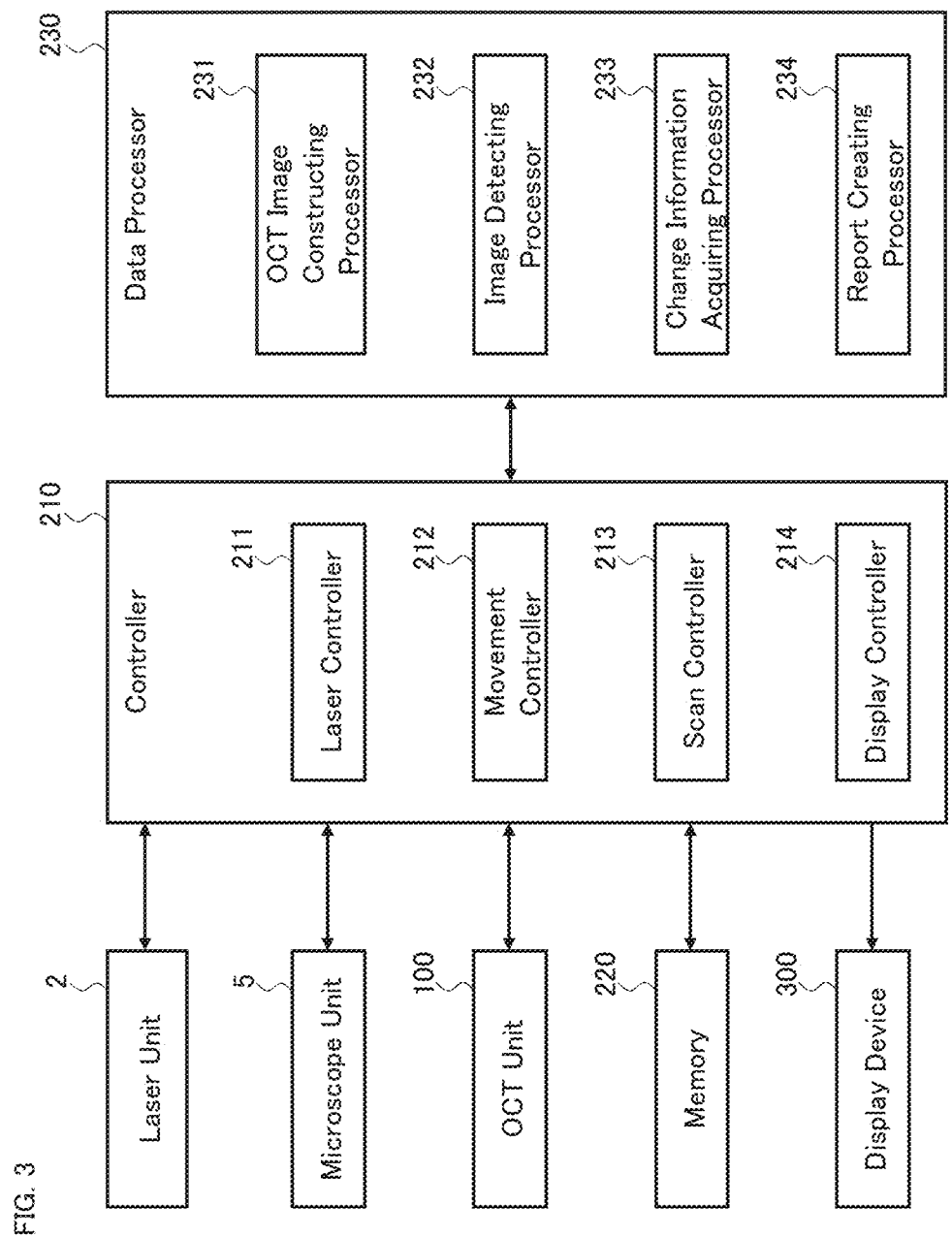
FIG. 3 is a schematic diagram illustrating the configuration of the photocoagulation apparatus according to the embodiment example.

FIG. 3 shows a configuration example of the processing system of the photocoagulation apparatus 1. The controller 210, the memory 220, and the data processor 230 are provided in the computer 200. The microscope unit 5 includes the illumination system 10, the observation system 20, and the photography system 30.

<Controller 210>

The controller 210 controls each element of the photocoagulation apparatus 1 (including the elements shown in FIG. 1 to FIG. 3). The controller 210 includes a processor and a storage. The functions of the controller 210 may typically be implemented by the cooperation of hardware including a processor and software including a control program. At least part of the functions of the controller 210 may be implemented by means of hardware including a control circuit.

The controller 210 includes the laser controller 211, the movement controller 212, the scan controller 213, and the display controller 214.

<Laser controller 211>

The laser controller 211 is configured to control the laser unit 2. The laser controller 211 performs control of the aiming light source and the treatment light source described above. For example, the laser controller 211 performs control of turning on and off of output and control of the output intensity (output power). In the case of employing a configuration capable of outputting a plurality of types of treatment light by using one or more treatment light sources, the laser controller 211 performs control to selectively output the plurality of types of treatment light.

<Movement controller 212>

The movement controller 212 is configured to control the OCT system 40 to move a scan target area. The scan target area is an area to which an OCT scan may be applied, that is, an area that is a target of the OCT scan. The scan target area is a control parameter that is internally set for OCT scanning. Further, the optical scanner 44 may be controlled according to the scan target area internally set. Note that the light source unit 101 does not output the light L0. The details of the control that can be executed by the movement controller 212 will be described later.

<Scan Controller 213>

The scan controller 213 is configured to control the OCT system 40 to actually apply an OCT scan to the retina Er. More specifically, the scan controller 213 applies an OCT scan to the retina Er, by a combination at least of control of the light source unit 101 and the optical scanner 44. The details of the control that can be executed by the scan controller 213 will be described later.

<Display Controller 214>

The display controller 214 is configured to display various kinds of information on the display device 300. In addition, the display controller 214 may perform various kinds of data processing relating to information to be displayed. The details of the control that can be executed by the display controller 214 will be described later.

<Memory 220>

The memory 220 stores various kinds of data. Further, the memory 220 stores various kinds of software, various kinds of parameters, and various kinds of templates for operating the photocoagulation apparatus 1.

The memory 220 of the present embodiment example stores an OCT image of the retina Er in advance. The OCT image is referred to as a reference OCT image. The reference OCT image is a three dimensional image of the fundus Ef that represents at least a three dimensional region of the retina Er. Typically, the reference OCT image is a wide area OCT image obtained by applying an OCT scan over a wide area of the retina Er. The wide area OCT image may be an image obtained by a wide angle OCT scan or a mosaic image obtained by a panoramic OCT scan. The panoramic OCT scan is a scan mode in which an OCT scan is sequentially applied to a plurality of regions of the fundus Ef, and the mosaic image is an image constructed by pasting together a plurality of OCT images respectively corresponding to the plurality of regions of the fundus Ef.

Further, the memory 220 of the present embodiment example stores a template of treatment reports in advance. A treatment report is a document (report) on the photocoagulation treatment having been conducted. In the present embodiment example, a treatment report is created by entering information in a template of a default format. Such a template is being stored in the memory 220.

The memory 220 typically includes a storage having a relatively large capacity such as a hard disk. Note that various kinds of data may be stored in a storage or an information processing apparatus located on a communication line. If this is the case, the memory 220 does not need to include the storage having a relatively large capacity. The same applies if a relatively large capacity storage is employed as a peripheral device of the photocoagulation apparatus 1.

<Data Processor 230>

The data processor 230 performs various kinds of data processing. For example, the data processor 230 may be configured to apply image processing and/or analysis processing to OCT image data, and/or, apply image processing and/or analysis processing to observation image data or photographed image data.

The function of the data processor 230 may typically be implemented by the cooperation of hardware including a processor and software including a data processing program. At least part of the function of the data processor 230 may be implemented by hardware including a data processing circuit.

The data processor 230 includes the OCT image constructing processor 231, the image detecting processor 232, the change information acquiring processor 233, and the report creating processor 234.

<October Image Constructing Processor 231>

The OCT image constructing processor 231 is configured to construct OCT image data from data acquired by the data acquisition system 130.

Typically, the OCT image constructing processor 231 constructs cross sectional image data based on data acquired by the data acquisition system 130. The image construction processing includes signal processing such as noise elimination (noise reduction), filtering, fast Fourier transform (FFT), and other processes as in conventional swept source OCT.

For example, the OCT image constructing processor 231 applies signal processing such as Fourier transform on the spectral distribution based on a sampling data group collected by the data acquisition system 130 for each series of wavelength scanning (for each A-line). This constructs reflection intensity profiles respectively for A-lines. Furthermore, the OCT image constructing processor 231 applies imaging processing to the reflection intensity profiles for the A-lines to construct image data. Arithmetic processes for the image data construction are the same as those of conventional swept source OCT.

Image data constructed by the OCT image constructing processor 231 is a data set including a group of a plurality of pieces of image data obtained by applying imaging processing to reflection intensity profiles at corresponding A-lines arranged in the area to which an OCT scan is applied.

An OCT scan applied to an A-line is referred to as an A-scan. Image data obtained by an A-scan is called A-scan image data. Further, the direction along the A-line is referred to as the A-scan direction. A collection of a plurality of A-scans arranged in a one dimensional direction orthogonal to the A-scan direction is referred to as a B-scan. The one dimensional direction orthogonal to the A-scan direction is referred to as the B-scan direction. Image data obtained by a B-scan is referred to as B-scan image data. B-scan image data is two dimensional cross sectional image data.

Image data constructed by the OCT image constructing processor 231 is, for example, one or more pieces of A-scan image data, one or more pieces of B-scan image data, or three dimensional image data. Three dimensional image data is image data represented by a three dimensional coordinate system, and typical examples thereof include stack data and volume data. Stack data is constructed by embedding a plurality of pieces of B-scan image data in a single three dimensional coordinate system. Volume data, also referred to as voxel data, is constructed by applying voxelization processing to stack data.

The OCT image constructing processor 231 may be configured to apply image processing to image data using any known image processing technique. For example, the OCT image constructing processor 231 may construct new image data by applying rendering to three dimensional image data. Examples of the rendering method include volume rendering, maximum intensity projection (MIP), minimum intensity projection (MinIP), surface rendering, and multi planar reconstruction (MPR). Further, the OCT image constructing processor 231 may be configured to construct projection data by projecting three dimensional image data in the A-line direction. In addition, the OCT image constructing processor 231 may be configured to construct a shadowgram by projecting part of three dimensional image data in the A-line direction. Here, the part of the three dimensional image data projected for the shadowgram construction is extracted by using segmentation, for example.

<Image Detecting Processor 232>

As described above, the photography system 30 performs moving image photography of the retina Er. By the moving image photography, a moving image of a predetermined frame rate is obtained. The moving image consists of time series images (multiple frames) captured sequentially at certain time intervals.

The photography system 30 of the present embodiment example performs moving image photography of the retina Er while the aiming light is being output from the laser unit 2. By operating the probe 4, the user projects the aiming light onto a desired position on the surface of the retina Er (i.e., onto a location to which the user desires to apply photocoagulation). A frame, which has been obtained while the aiming light is being projected onto the surface of the retina Er, contains an image of the aiming light. The image detecting processor 232 repeats detection of an image of the aiming light from a moving image acquired while the aiming light is being output from the laser unit 2.

While the aiming light is being output from the laser unit 2, the photography system 30 outputs frames at certain time intervals, and these frames are sequentially sent to the image detecting processor 232. The image detecting processor 232 analyzes each frame and detects an image of the aiming light contained in that frame. As a result, a time change (temporal change, time course) of the position of the image of the aiming light can be obtained.

The processing executed by the image detecting processor 232 to detect an image of the aiming light from a frame, typically includes analysis of pixel values. Examples of the pixel value analysis include thresholding related to brightness and analysis based on wavelength.

The thresholding related to brightness may include, for example, a process of comparing the brightness value of each pixel in a frame with a threshold set in advance, and a process of selecting pixels each having a brightness value equal to or greater than the threshold. The threshold may be set according to the intensity of the illumination light (light amount), the intensity of the aiming light (light amount), or the like. Note that in the case where one or both of the intensity of the illumination light and the intensity of the aiming light is or are variable, the threshold may be determined in accordance with a set value of the intensity.

In general, the optic nerve head is depicted in high brightness in a front image of the fundus. The image detecting processor 232 may discriminate between the image of the optic nerve head and the image of the aiming light, based on the size and/or the position of an image depicted in a frame, for example.

Then, a description will be given of the analysis based on wavelength. Typically, a frame is an image acquired using illumination light, which is infrared light (then, the frame is an infrared image), and the aiming light contains a visible light component. Further, the image sensor 33 has sensitivity to both a visible light component and an infrared light component. The image detecting processor 232 detects an image depicted with a visible light component in a frame, as an image of the aiming light.

<Change Information Acquiring Processor 233>

The change information acquiring processor 233 is configured to acquire, from two or more OCT images acquired at different times (different time points), change information representing a tissue change in the retina Er caused by the treatment light. The change information includes, for example, any of the following types of information; a position (location) where a tissue change has occurred, a distribution of positions (locations) where tissue changes have occurred, and the size (magnitude), shape, and degree of a tissue change.

The change information acquiring processor 233 may execute a comparison between an OCT image acquired before the commencement of a current photocoagulation treatment (i.e., reference OCT image) and an OCT image acquired after the application of the treatment light to a certain location in the retina Er, thereby identifying a tissue change in that location caused by the treatment light. Then, the change information acquiring processor 233 may generate change information including a result of the tissue change identification.

In addition, by comparing the reference OCT image and an OCT image acquired after the completion of the current photocoagulation treatment with each other, the change information acquiring processor 233 may identify a tissue change in the retina Er caused by the current photocoagulation treatment and then generate change information including a result of the tissue change identification.

Further, the change information acquiring processor 233 may compare an OCT image acquired after the application of the treatment light to a certain location in the retina Er and an OCT image acquired after the completion of the current photocoagulation treatment with each other. With this, the change information acquiring processor 233 may compare an initial tissue change caused by the treatment light applied to that location and a subsequent tissue change with each other, and then generate change information including a result of the tissue change comparison. In other words, the change information acquiring processor 233 may be capable of acquiring change information representing a time change in a tissue change caused by the treatment light.

In some examples, the change information acquiring processor 233 may be configured to obtain a tissue change in the retina Er in the following manner. First, the change information acquiring processor 233 performs position matching (registration) between two or more OCT images acquired at different times (different time points) from substantially the same position (substantially the same location) of the retina Er. Next, the change information acquiring processor 233 constructs an image representing a change between these OCT images by calculating a difference between or a ratio of two or more OCT images to which the registration has been applied. For example, the change information acquiring processor 233 may construct motion contrast data from two or more OCT images to which the registration has been conducted. Subsequently, the change information acquiring processor 233 may obtain a tissue change in the retina Er from the motion contrast data constructed. A method or technique for constructing motion contrast data is known, and is disclosed in, for example, Japanese Unexamined Patent Application Publication No. 2015-131107 and Japanese Unexamined Patent Application Publication No. 2016-010656.

<Report Creating Processor 234>

The report creating processor 234 reads out a template of a treatment report from the memory 220 and enters data in the template based on the information acquired by the change information acquiring processor 233.

The template is provided with input fields (entry fields) corresponding to various kinds of input items (entry items). As described above, the change information acquiring processor 233 acquires information on various kinds of items such as a position where a tissue change has occurred, a distribution of such positions, the size of a tissue change, the shape of a tissue change, and the degree of a tissue change, and the like. The report creating processor 234 then identifies a correspondence relationship between the items of information acquired by the change information acquiring processor 233 and the items in the template. Subsequently, the report creating processor 234 identifies a field in the template into which corresponding information is to be entered, and then enters the corresponding information in the field identified.

The report creating processor 234 may input data into the template based on information other than the information acquired by the change information acquiring processor 233. For example, the report creating processor 234 may enter, in the template, an image acquired by the photography system 30, an image acquired by the OCT system 40, information input by the user (doctor), or the like. In addition, the user may delete or edit the data that has been entered by the report creating processor 234.

<Usage Mode>

Figure 4B:
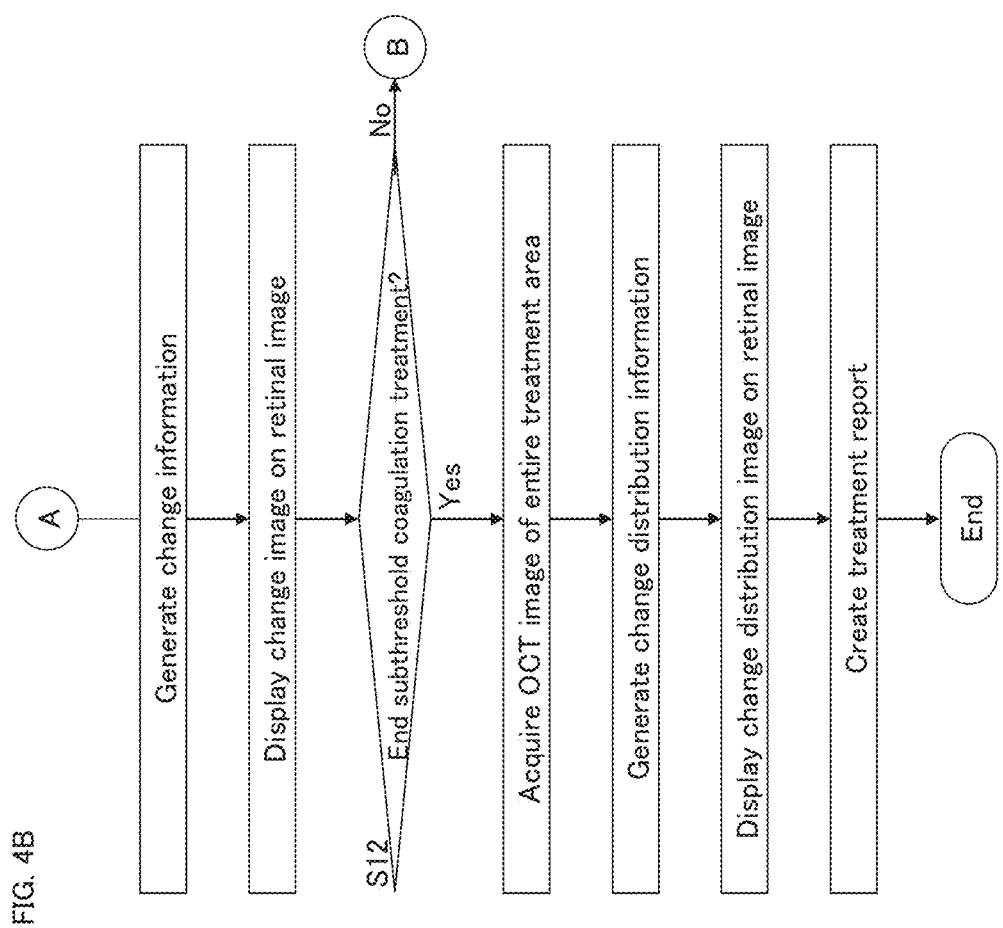
FIG. 4B is a flowchart illustrating a usage mode of the photocoagulation apparatus according to the embodiment example.

Some usage modes of the photocoagulation apparatus 1 will be described. FIG. 4A and FIG. 4B show the flow of an exemplary usage mode.

(S1: Acquire Reference OCT Image)

Prior to the commencement of photocoagulation treatment (subthreshold coagulation treatment), the photocoagulation apparatus 1 acquires a reference OCT image of the fundus Ef of the patient's eye E (the retina Er). The reference OCT image is a wide area OCT image of the retina Er. The reference OCT image is stored in the memory 220.

OCT scanning for constructing the reference OCT image is performed by the photocoagulation apparatus 1 or another OCT apparatus. In the case where the photocoagulation apparatus 1 performs the OCT scanning, the photocoagulation apparatus 1 (the OCT image constructing processor 231) may also carry out the construction of the reference OCT image. In the case where another OCT apparatus performs the OCT scanning, the photocoagulation apparatus 1 or an apparatus other than the photocoagulation apparatus 1 carries out the construction of the reference OCT image.

Prior to the commencement of subthreshold coagulation treatment, the photocoagulation apparatus 1 may further perform acquisition of a retinal image. Note that the photocoagulation apparatus 1 may acquire a retinal image at an arbitrary time after the commencement of subthreshold coagulation treatment. The retinal image thus acquired is stored in the memory 220.

The retinal image is acquired by the photocoagulation apparatus 1 or another ophthalmic imaging apparatus. Examples of the retinal image that can be acquired by the photocoagulation apparatus 1 of the present embodiment example include an image of the retina Er acquired by the photography system 30 and a front image of the retina Er acquired by the OCT system 40 and the OCT image constructing processor 231.

More generally, the retinal image may be any of the following: (1) an image of the retina Er acquired by a fundus camera, such as a gray scale image, a color image, a morphological image, and a fluorescent contrast image; (2) an image of the retina Er acquired by a scanning laser ophthalmoscope (SLO), such as a gray scale image, a color image, a morphological image, and a fluorescent contrast image; (3) an image of the retina Er acquired by a surgical microscope; (4) an image of the retina Er acquired by a slit lamp microscope; (5) a front image of the retina Er acquired by using OCT, such as a morphological image and a blood vessel emphasized image (also referred to as an OCT angiogram and a motion contrast image).

(S2: Start Subthreshold Coagulation Treatment)

After acquiring the reference OCT image (and the retinal image), the subthreshold coagulation treatment is commenced.

(S3: Start Observation and Moving Image Photography of Fundus)

In response to the commencement of the subthreshold coagulation treatment, the controller 210 turns on the illumination light source 11 of the illumination system 10 and activates the image sensor 33. As a result, observation of the fundus Ef (the retina Er) using the observation system 20 may be started, and moving image photography of the fundus Ef (the retina Er) by the photography system 30 may be started.

(S4: Start Projection of Aiming Light)

The user inserts the probe 4 into the patient's eye E. The controller 210 controls the laser unit 2 to start output of the aiming light.

(S5: Start Detection of Image of Aiming Light)

The controller 210 activates the image detecting processor 232. The image detecting processor 232 executes processing of detecting images of the aiming light from frames sequentially obtained by the moving image photography started in the step S3. Typically, the image detecting processor 232 processes each of the frames obtained by the moving image photography. Alternatively, the controller 210 may select frames by thinning out the frames obtained by the moving image photography and send the selected frames to the image detecting processor 232.

Figure 5A:
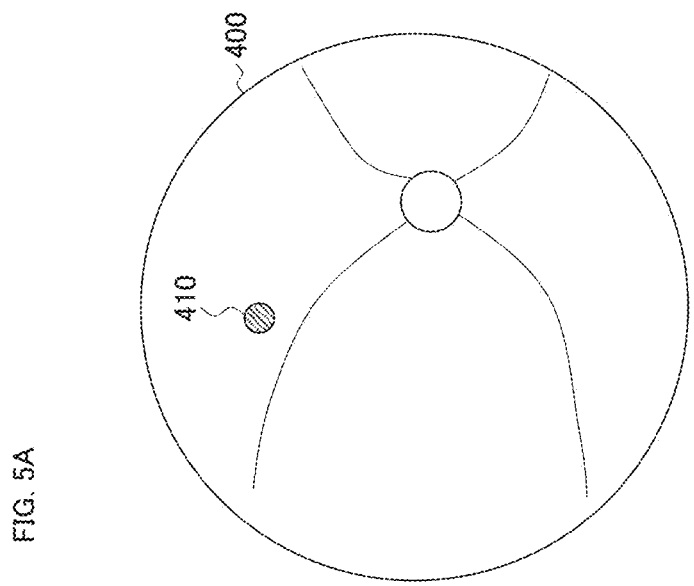
FIG. 5A is a schematic diagram for describing a usage mode of the photocoagulation apparatus according to the embodiment example.

As shown in FIG. 5A, the image of the aiming light (aiming light image) 410 is depicted in the frame 400 as a typical example. The image detecting processor 232 detects the aiming light image 410 from the frame 400. As a result of this, the position (coordinates) of the aiming light image 410 in the frame 400 may be determined. The position of the aiming light image 410 is represented, for example, as the coordinates of a feature point (e.g., center or center of gravity) of the aiming light image 410.

(S6: Start Movement of Scan Target Area)

The movement controller 212 moves a scan target area in such a way that the scan target area becomes to include an application position of the aiming light to the retina Er, by controlling the OCT system 40 based on the image of the aiming light detected by the image detecting processor 232.

Figure 5B:
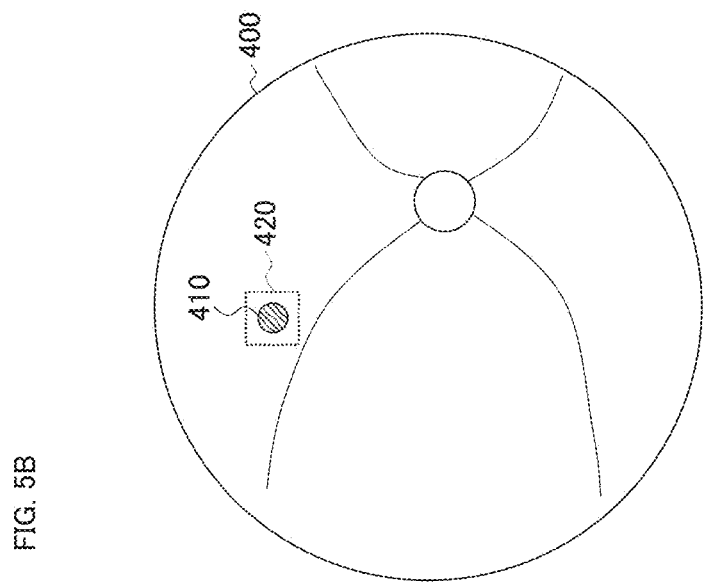
FIG. 5B is a schematic diagram for describing a usage mode of the photocoagulation apparatus according to the embodiment example.

In the case where the position of the aiming light image 410 in the frame 400 shown in FIG. 5A has been determined, the movement controller 212 sets a vicinity (neighborhood) of the determined position as the scan target area. Here, the vicinity is a region that includes the determined position, and is a sufficiently small region as compared with the scan area of the wide area OCT image. An example of the scan target area set for the aiming light image 410 is shown in FIG. 5B (the area denoted by the reference character 420).

In the present embodiment example, the optical axis of the photography system 30 and the optical axis of the OCT system 40 are arranged coaxially via the beam splitter 31. Such an optical arrangement gives a natural correspondence relationship of positions (coordinates) between an image acquired by the photography system 30 and data collected by the OCT system 40. For example, the center of an image acquired by the photography system 30 (optical axis position) and the scan center of the optical scanner 44 of the OCT system 40 (center of a scannable area) coincide with each other. For example, the movement controller 212 moves and places the center of the scan target area to and at the center (or the center of gravity) of the aiming light image 410.

(S7: User Instructs Application of Treatment Light)

The user issues an instruction to start application of treatment light while the aiming light is being projected onto a desired location on the retina Er. The instruction is issued, for example, by operating an application button or a foot switch (not shown in the drawings).

(S8: Apply Treatment Light)

The laser controller 211 receives the instruction for treatment light application and then controls the laser unit 2 to output treatment light. The treatment light output is applied to the retina Er via the optical fiber 3 and the probe 4.

Here, an application condition(s) of the treatment light may be stored in the memory 220. Examples of the application condition include wavelength, intensity, application time, spot size, duty ratio (or duty cycle), and pulse width.

(S9: Acquire OCT Image Near Application Position)

After the application of the treatment light, the scan controller 213 controls the OCT system 40 to apply an OCT scan to the scan target area at a time of reception of the application instruction. The OCT image constructing processor 231 constructs an OCT image based on data acquired by the OCT scan. The OCT scan is typically performed immediately after the application of the treatment light.

Figure 5C:
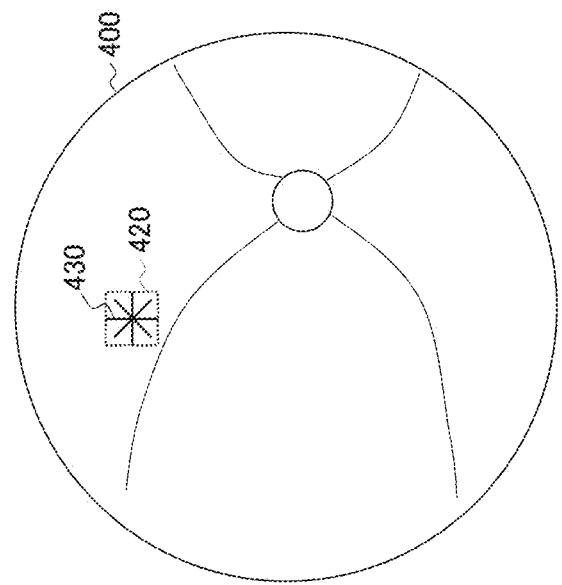
FIG. 5C is a schematic diagram for describing a usage mode of the photocoagulation apparatus according to the embodiment example.

The OCT scan may be, for example, a three dimensional scan (raster scan) for the scan target area 420 shown in FIG. 5B, or a radial scan 430 shown in FIG. 5C. The radial scan 430 is set within the scan target area 420.

(S10: Generate Change Information)

The change information acquiring processor 233 generates change information representing a tissue change in the retina Er caused by the treatment light applied in the step S8, by comparing the reference OCT image acquired in the step S1 and the OCT image acquired in the step S9 with each other.

(S11: Display Change Image on Retinal Image)

The display controller 214 displays a change image based on the change information generated in the step S10 on the display device 300 together with a retinal image. Typically, the display controller 214 prepares the first layer and the second layer that is overlaid on the first layer. In addition, the display controller 214 displays the retinal image on the first layer and the change image on the second layer.

The retinal image may be, for example, any of the retinal images acquired in the step S1. Further, the change information may include, for example, any of the position of the tissue change, the distribution of the tissue changes, the size of the tissue change, the shape of the tissue change, and the degree of the tissue change, as described above. The position of the tissue change is represented by, for example, a display position of the change image with respect to the retinal image. The distribution of the tissue changes is represented by, for example, a distribution (map) of a plurality of change images in the retinal image. The size of the tissue change is represented by, for example, the size of the change image in the retinal image. The shape of the tissue change is represented by, for example, the shape (outer shape) of the change image. The degree of the tissue change is represented by, for example, the display color of the change image.

Figure 6A:
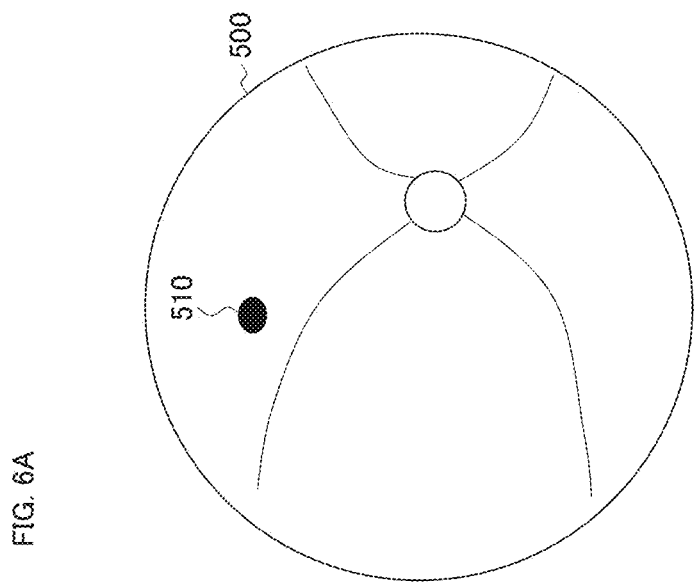
FIG. 6A is a schematic diagram for describing a usage mode of the photocoagulation apparatus according to the embodiment example.

FIG. 6A shows an example of the information displayed in the step S11. In the present example, the retinal image 500 is a front image of the retina Er of any type, and the change image 510 represents the position, size, and shape of the tissue change.

The display controller 214 may read out the application condition applied in the step S8 (e.g., wavelength, intensity, application time, spot size, duty ratio, pulse width) from the memory 220, and then display the application condition together with the change image 510. For example, as shown in FIG. 6B, the application condition is presented in the balloon 520 that points to the change image 510. In some other examples, the application condition may be popped up in response to an operation of designating (e.g., clicking) the change image 510.

(S12: End Subthreshold Coagulation Treatment?)

A series of the steps S7 to S12 is repeated until the completion of the subthreshold coagulation treatment (S12: No). Typically, each time the series of the steps S7 to S12 is repeated, treatment light is applied to a new location of the retina Er (S8), an OCT image of the vicinity of the new application location is acquired (S9), new change information is generated (S10), and a new change image is displayed in addition to previous change images (S11).

FIG. 6C shows an example of the information displayed in the step S11 after the series of the steps S7 to S12 is repeated a plurality of times. In the present example, the change image group 530 corresponding to a plurality of treatment light applications is displayed on the retinal image 500. It should be noted that each change image represents a tissue change in a deep part of the retina, that is, each change image does not represent a coagulation spot on the retinal surface.

(S13: Acquire OCT Image of Entire Treatment Area)

After performing the applications of the treatment light to the plurality of positions on the retina Er, the scan controller 213 applies an OCT scan to an area including all of the plurality of application positions. The OCT image constructing processor 231 constructs an OCT image from the data acquired by the OCT scan performed on the area.

Figure 7A:
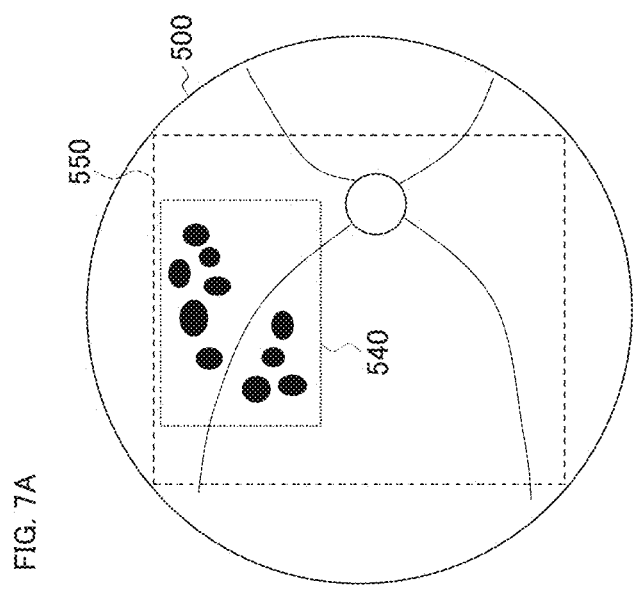
FIG. 7A is a schematic diagram for describing a usage mode of the photocoagulation apparatus according to the embodiment example.

FIG. 7A shows an example of the OCT scan area in the step S13. In the case where the plurality of change images shown in FIG. 6C (the change image group 530) is displayed, the scan controller 213 applies an OCT scan to the area 540 that includes all of these change images. Note that the area 550 denotes a scan area corresponding to the reference OCT image acquired in the step S1.

While the single area 540 (connected region) that includes all of the change images is employed in the present example, two or more areas (two or more connected regions) that include all of the change images may be employed in some other examples. For example, in the case where the plurality of change images shown in FIG. 6C (the change image group 530) is displayed, the scan controller 213 may employ the two areas 561 and 562 shown in FIG. 7B.

(S14: Generate Change Distribution Information)

The change information acquiring processor 233 compares the reference OCT image acquired in the step S1 and the OCT image acquired in the step S13 with each other. Based on the comparison, the change information acquiring processor 233 generates the first change distribution information representing a distribution of the tissue changes in the retina Er over the scan area applied in the step S13. The first change distribution information represents the tissue changes in the period from a time point before the application of the treatment light up to a time point at which the OCT scan of the step S13 has been performed.

Further, the change information acquiring processor 233 may compare the OCT image acquired in the step S9 and the OCT image acquired in the step S13 with each other. Based on the comparison, the change information acquiring processor 233 may generate the second change distribution information representing a distribution of the tissue changes in the retina Er over the area that includes all of the treatment light application positions. The second change distribution information represents the tissue changes in the period from a time point immediately after the application of the treatment light up to a time point at which the OCT scan of the step S13 has been performed.

Each of the first change distribution information and the second change distribution information may represent any of the positional distribution of tissue changes caused by the treatment light, the sizes of the tissue changes, the shapes of the tissue changes, the degrees of the tissue changes, and the like.

(S15: Display Change Distribution Image on Retinal Image)

The display controller 214 displays the first change distribution image based on the first change distribution information generated in the step S14 on the display device 300 together with a retinal image. The retinal image may be the same image of the same type as the retinal image displayed in the step S11, may be a different image of the same type, or may be an image of a different type. The first change distribution image is a visualization of the tissue changes in the period from a time point before the application of the treatment light up to a time point at which the OCT scan of the step S13 has been performed.

In the case where the second change distribution information has been acquired in the step S14, the display controller 214 may display the second change distribution image based on the second change distribution information on the display device 300 together with a retinal image. The retinal image may be the same image of the same type as the retinal image displayed in the step S11, may be a different image of the same type, or may be an image of a different type. The second change distribution image is a visualization of the tissue changes in the period from a time point immediately after the application of the treatment light up to a time point at which the OCT scan of the step S13 has been performed.

(S16: Create Treatment Report)

The report creating processor 234 reads out a template of a treatment report from the memory 220 and enters data into the template based at least on the information acquired by the change information acquiring processor 233.

In the present example, the report creating processor 234 may enter any of the following types of information into the template, and may enter data obtained from any of the following types of information into the template: (1) the reference OCT image acquired in the step S1; (2) the moving image or a frame therein obtained by the moving image photography started in the step S3; (3) a result of the detection of the images of the aiming light started in the step S5; (4) history of the movement of the scan target area started in the step S6; (5) the OCT image acquired in the step S9; (6) the change information generated in the step S10; (7) the change image and/or the retinal image displayed in the step S11; (8) the OCT image acquired in the step S13; (9) the change distribution information generated in the step S14; and (10) the change distribution image and/or the retinal image displayed in the step S15.

The report creating processor 234 may also enter, into the template, data from the electronic medical record of the patient, an image of the patient's eye E acquired by another apparatus, or the like.

The treatment report created in the step S16 is typically sent to a database such as an electronic medical record system and saved on the database. This terminates the usage mode of the present example (end).

<Effects>

Some effects of the photocoagulation apparatus 1 will be described.

The photocoagulation apparatus 1 is used to apply subthreshold coagulation to the retina Er via the probe 4 inserted in the eye. The photocoagulation apparatus 1 includes: the laser unit 2, the optical fiber 3, and the probe 4 (the light guiding system); the photography system 30; the image detecting processor 232; the OCT system 40; the movement controller 212; the memory 220 (the first memory); the scan controller 213; the OCT image constructing processor 231 (the image constructing processor); the change information acquiring processor 233; and the display controller 214.

The light guiding system is configured to guide the aiming light and the treatment light generated by the laser unit 2 to the retina Er via the probe 4.

The photography system 30 is configured to perform moving image photography of the retina Er at least while (at least during a period when) the light guiding system is guiding the aiming light.

The image detecting processor 232 is configured to repeatedly detect an image of the aiming light from a moving image acquired by the moving image photography.

The OCT system 40 is configured to apply an OCT scan to the retina Er.

The movement controller 212 is configured to move the scan target area to include an application position of the aiming light on the retina Er, by sequentially controlling the OCT system 40 based on the image of the aiming light sequentially detected by the image detecting processor 232.

The first memory is configured to store the first OCT image (the reference OCT image) of the retina Er in advance.

The scan controller 213 is configured to control the OCT system 40, after the light guiding system guides the treatment light upon receiving an instruction from the user, to apply an OCT scan to the scan target area at a time of reception of the instruction. The image constructing processor is configured to construct the second OCT image from data acquired by the OCT scan.

The change information acquiring processor 233 is configured to acquire change information representing a tissue change in the retina Er caused by the treatment light, by comparing the first OCT image and the second OCT image with each other.

The display controller 214 is configured to display a change image based on the change information on the display device 300 together with a retinal image.

The display device 300 may be in any form. For example, the display device 300 may be a general display, a display mounted on the photocoagulation apparatus 1, a head-up display used for stereoscopic observation of the retina Er, or a display mounted on polarized glasses worn for stereoscopic viewing with the head-up display.

According to the photocoagulation apparatus 1 as described above, the state of tissue changes caused by the treatment light can be visualized in real time by performing an OCT scan after the application of the treatment light for subthreshold coagulation while moving the target area of the OCT scan in accordance with the position transition of the image of the aiming light formed in the retina Er. In other words, the photocoagulation apparatus 1 is capable of visualizing in real time and appropriately presenting to the user, the state of tissue changes in a deep part of the retina that occur in the subthreshold coagulation treatment. Subthreshold coagulation can also be properly carried out even in the case of using the probe 4 inserted into the eye.

The scan controller 213 of the present embodiment example may be configured to control the OCT system to perform an OCT scan each time the light guiding system guides the treatment light. If this is the case, the image constructing processor may construct the second OCT image each time the OCT scan is performed by the OCT system 40. Further, the change information acquiring processor 233 may acquire the change information each time the second OCT image is constructed by the image constructing processor. In addition, the display controller 214 may update the displayed change image presented to the user together with the retinal image each time the change information is acquired by the change information acquiring processor 233.

Such a configuration makes it possible to update the display of a change image representing a tissue change in a deep part of the retina each time treatment light is applied to the retina Er. For example, a change image representing a tissue change in a deep part of the retina caused by another treatment light can be added each time treatment light is newly applied to the retina Er. Therefore, the photocoagulation apparatus 1 can visualize in real time and appropriately present to the user, the state of tissue changes in a deep part of the retina that occur in the subthreshold coagulation treatment.

The scan controller 213 of the present embodiment example may be configured to control the OCT system 40 to perform an OCT scan immediately after the light guiding system guides the treatment light.

Such a configuration makes it possible to achieve both applications of the treatment light at short time intervals and real time visualization of the state of tissue changes in a deep part of the retina.

The scan controller 213 of the present embodiment example may be configured to control the OCT system 40, after the treatment light is applied to each of a plurality of positions (locations) on the retina Er, to apply an OCT scan to an area that includes all of the plurality of positions. If this is the case, the image constructing processor may construct the third OCT image from data acquired by the OCT scan applied to that area. Further, the change information acquiring processor 233 may acquire the first change distribution information representing a distribution of tissue changes in the retina Er in that area, by comparing the first OCT image and the third OCT image with each other. In addition, the display controller 214 may control the display device 300 to display the first change distribution image based on the first change distribution information together with a retinal image.

According to such a configuration, the photocoagulation apparatus 1 becomes capable of acquiring an OCT image of the entire treatment area after subthreshold coagulation treatment is performed on a plurality of positions on the retina Er, and then visualizing the distribution and/or state of tissue changes. Here, the first change distribution information represents tissue changes in a deep part of the retina between before and after the subthreshold coagulation treatment.

In the present embodiment example, each of a plurality of scan target areas respectively corresponding to the plurality of positions on the retina Er, to each of which the subthreshold coagulation is applied, may be smaller than the area that includes all of the plurality of positions, that is, may be smaller than the area on which an OCT scan is performed after the subthreshold coagulation treatment.

According to such a configuration, the OCT scan area after the application of the treatment light is small, and therefore the duration of time required for the OCT scan can be shortened. This makes it possible to achieve both applications of treatment light at short time intervals and real time visualization of the state of a tissue change in a deep part of the retina.

The change information acquiring processor 233 of the present embodiment example may be configured to acquire the second change distribution information representing a distribution of tissue changes in the retina Er over the area that includes all of the plurality of positions on the retina Er, to each of which the subthreshold coagulation is applied, by comparing the second OCT image and the third OCT image with each other. The display controller 214 may control the display device 300 to display the second change distribution image based on the second change distribution information together with a retinal image.

According to such a configuration, the photocoagulation apparatus 1 becomes capable of acquiring an OCT image of the entire treatment area after subthreshold coagulation treatment is performed on a plurality of positions on the retina Er, and then visualizing the distribution and state of tissue changes. Here, the second change distribution information represents tissue changes in a deep part of the retina between immediately after application of the treatment light to each of the plurality of positions on the retina Er and after the subthreshold coagulation treatment.

The change information acquiring processor 233 of the present embodiment example may be configured to construct motion contrast data from two or more OCT images acquired from substantially the same position (substantially the same location) of the retina Er at different times, and determine a tissue change in the retina Er from the motion contrast data.

Such a configuration makes it possible to acquire any of the change information, the first change distribution information, and the second change distribution information, by using a motion contrast technique like OCT angiography.

The display controller 214 of the present embodiment example may be configured to display the retinal image on the first layer, and displays, on the second layer overlaid on the first layer, an image based on information acquired by the change information acquiring processor 233.

Such a configuration makes it possible to provide a specific method or technique for displaying any one or more of the change image, the first change distribution image, and the second change distribution image on the retinal image. In addition, such a configuration makes it possible to facilitate the update of the change image and the like.

The display controller 214 in the present embodiment example may be configured to display the application condition of the treatment light guided by the light guiding system together with the image based on the information acquired by the change information acquiring processor 233.

According to such a configuration, the photocoagulation apparatus 1 becomes capable of providing to the user the application condition (e.g., wavelength, intensity, application time, spot size, duty ratio, pulse width) of the treatment light applied to the retina Er together with any of the change image, the first change distribution image, and the second change distribution image.

The photocoagulation apparatus 1 of the present embodiment example may further include the second memory (the memory 220) and the report creating processor 234. The second memory is configured to store a template of a treatment report in advance. The report creating processor 234 may enter data in the template based at least on the information acquired by the change information acquiring processor 233.

Such a configuration allows the photocoagulation apparatus 1 to automatically create a treatment report on the basis of any of the change information, the first change distribution information, the second change distribution information, the change image, the first change distribution image, and the second change distribution image, and/or, on the basis of data based on any of them.

The retinal image of the present embodiment example may be any of an image of the retina Er acquired by a fundus camera, an image of the retina Er acquired by a scanning laser ophthalmoscope, an image of the retina Er acquired by a surgical microscope, an image of the retina Er acquired by a slit lamp microscope, and a front image of the retina Er acquired by using OCT.

According to such a configuration, the photocoagulation apparatus 1 can display any of the change image, the first change distribution image, and the second change distribution image together with a retinal image of a desired type.

<First Modification Example of Photocoagulation Apparatus>

A photocoagulation apparatus of the first modification is configured to be capable of presenting various kinds of information within the observation field of view of a stereoscopic image obtained by a microscope. For example, the photocoagulation apparatus of the first modification may be capable of presenting, within the observation field of view of a stereoscopic image obtained by a microscope, any of a retinal image, a change image, the first change distribution image, the second change distribution image, the application condition of the treatment light, and the like.

Figure 8:
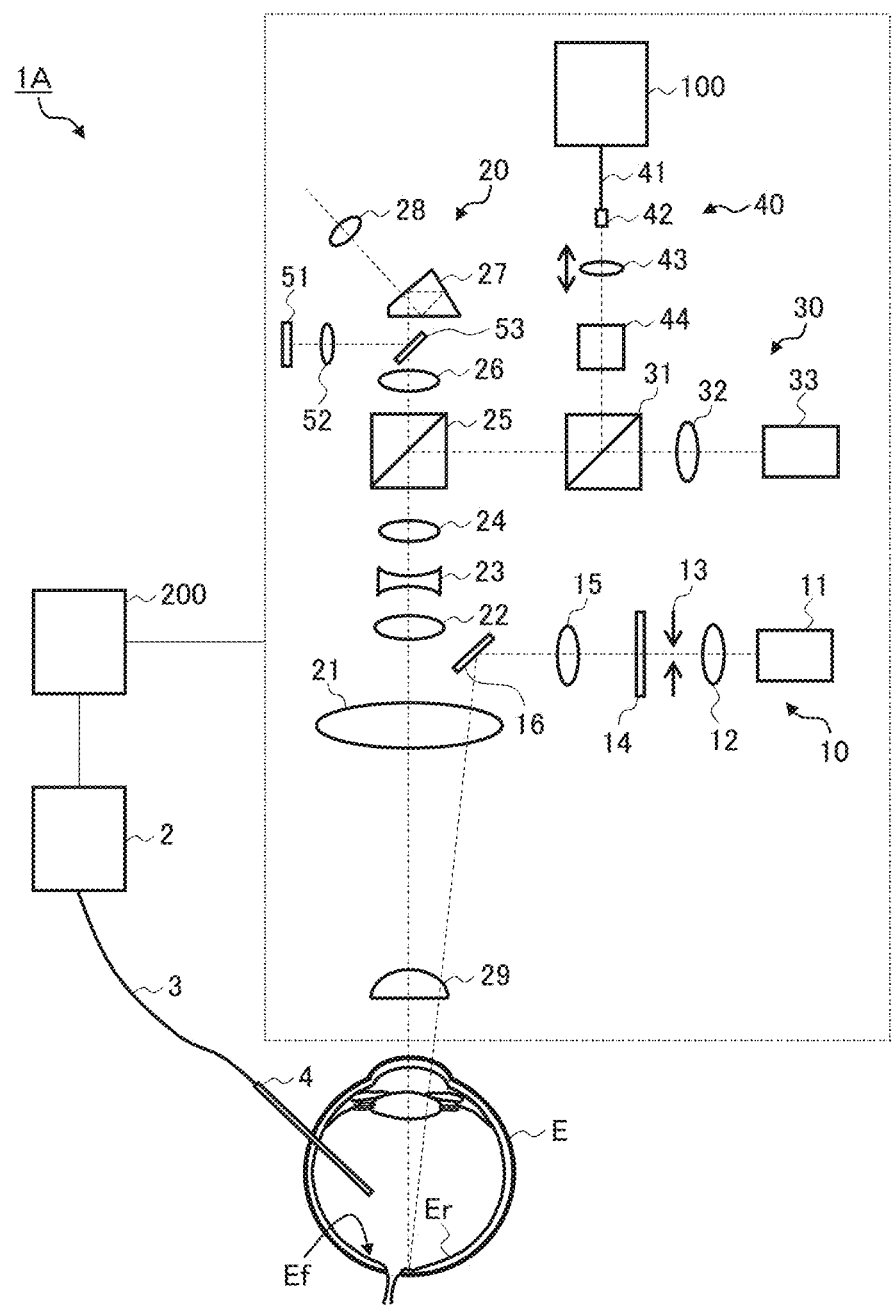
FIG. 8 is a schematic diagram illustrating the configuration of the photocoagulation apparatus according to the modification example.

FIG. 8 shows an example of a configuration that may be employed to realize such a function. The same or similar elements as or to those of the photocoagulation apparatus 1 according to the above embodiment example are denoted by the same reference characters, and the descriptions thereof will be omitted unless otherwise mentioned.

The photocoagulation apparatus 1A shown in FIG. 8 is different from the photocoagulation apparatus 1 according to the above embodiment example in that the photocoagulation apparatus 1A additionally includes the display device 51, the imaging lens 52, and the beam splitter 53, and does not include the display device 300 of the photocoagulation apparatus 1.

In other words, the photocoagulation apparatus 1A is used to apply subthreshold coagulation to the retina Er via the probe 4 inserted into the eye and includes the followings; the laser unit 2 and the optical fiber 3 (the light guiding system), the photography system 30, the image detecting processor 232, the OCT system 40, the movement controller 212, the memory 220 (the first memory), the scan controller 213, the OCT image constructing processor 231 (the image constructing processor), the change information acquiring processor 233, and the display controller 214. These elements are the same as the photocoagulation apparatus 1 according to the embodiment example described above.

In addition to them, the photocoagulation apparatus 1A includes the display device 51 in place of the display device 300, and also includes the imaging lens 52 and the beam splitter 53. Further, the photocoagulation apparatus 1A explicitly uses the observation system 20. The observation system 20 includes an optical system configured for the user to observe a magnified image of the retina Er via the eyepiece 28.

The imaging lens 52 and the beam splitter 53 are disposed in an optical path starting from the display device 51.

The beam splitter 31 (an optical path coupling member) is, for example, a half mirror, and is configured and arranged to couple the optical path starting from the display device 51 with the optical path of the observation system 20 that continues up to the eyepiece 28.

The display controller 214 displays a change image based on the change information acquired by the change information acquiring processor 233 on the display device 51 together with a retinal image. Further, the display controller 214 updates display of the change image presented to the user together with the retinal image each time the change information is acquired by the change information acquiring processor 233.

The display controller 214 controls the display device 51 to display the first change distribution image based on the first change distribution information acquired by the change information acquiring processor 233 together with a retinal image. Further, the display controller 214 controls the display device 51 to display the second change distribution image based on the second change distribution information acquired by the change information acquiring processor 233 together with a retinal image.

The display controller 214 displays the retinal image on the first layer, and displays, on the second layer overlaid on the first layer, an image based on information acquired by the change information acquiring processor 233. The information acquired by the change information acquiring processor 233 may be any of the change image, the first change distribution image, and the second change distribution image, for example.

The display controller 214 displays the application condition (e.g., wavelength, intensity, application time, spot size, duty ratio, pulse width) of the treatment light guided by the light guiding system together with an image generated based on the information acquired by the change information acquiring processor 233 (e.g., the change image, the first change distribution image, the second change distribution image).

According to such a configuration, the photocoagulation apparatus 1A becomes capable of presenting various kinds of information within the observation field of view of the stereoscopic image provided to the user through the observation system 20.

Any of the configurations (elements) and/or any of the functions of the photocoagulation apparatus 1 according to the above embodiment example may be combined with the photocoagulation apparatus 1A according to the present modification example. Further, any known method or technique may be combined with the photocoagulation apparatus 1A according to the present modification example.

<Second Modification Example of Photocoagulation Apparatus>

The photocoagulation apparatus 1 according to the above embodiment example may be used to apply subthreshold coagulation to the retina Er via the probe 4 inserted into the eye. On the other hand, the present modification example will give a description of the photocoagulation apparatus 1B that can be used for performing subthreshold coagulation without inserting a probe into the eye.

Figure 9:
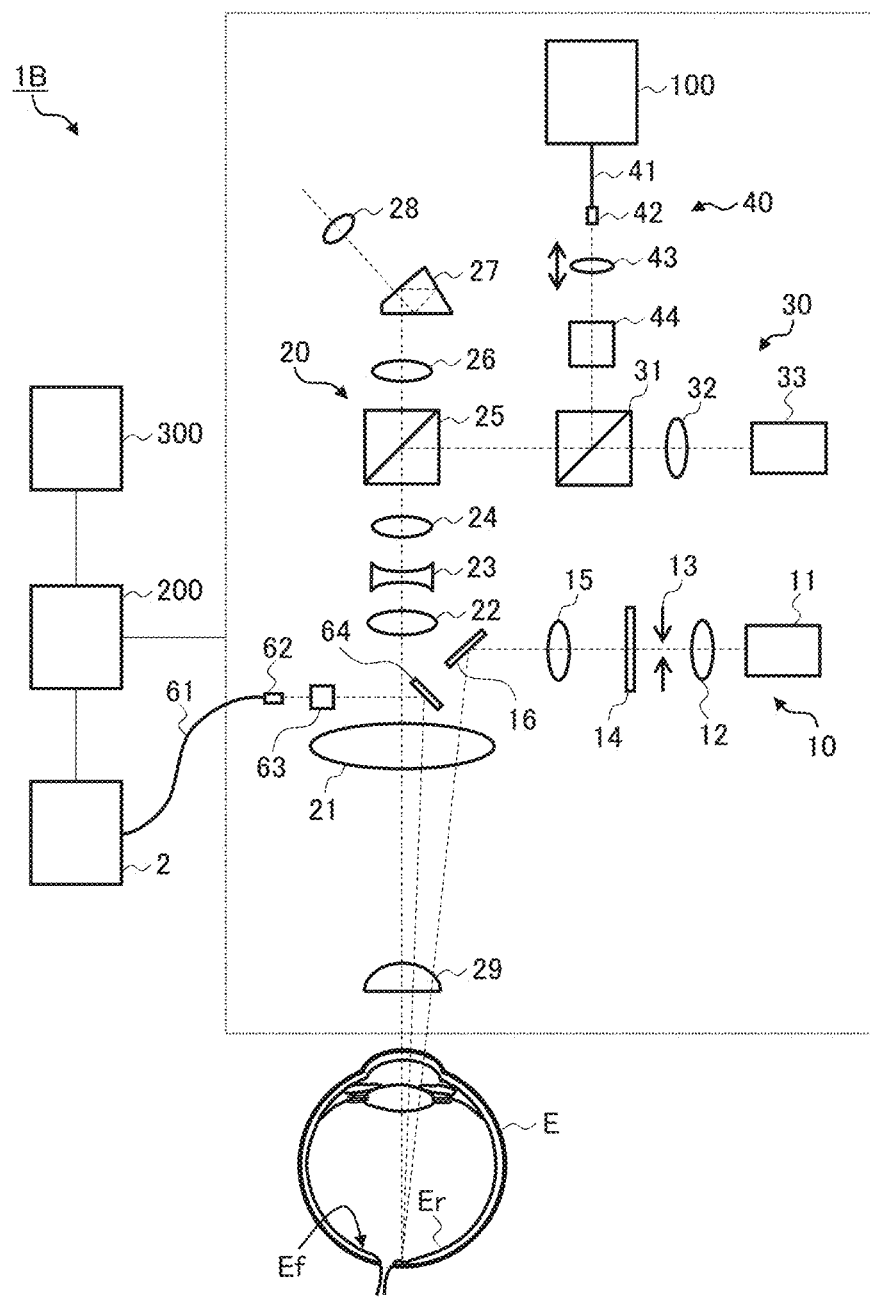
FIG. 9 is a schematic diagram illustrating the configuration of the photocoagulation apparatus according to the modification example.

FIG. 9 shows an example of a configuration that may be employed for subthreshold coagulation without inserting a probe into the eye. The same or similar elements as or to those of the photocoagulation apparatus 1 according to the above embodiment example are denoted by the same reference characters, and the descriptions thereof will be omitted unless otherwise mentioned.

The photocoagulation apparatus 1B shown in FIG. 9 is different from the photocoagulation apparatus 1 according to the above embodiment example in that the photocoagulation apparatus 1B additionally includes the optical fiber 61, the collimator lens unit 62, the optical scanner 63, and the deflection member 64, and does not include the optical fiber 3 and the probe 4 of the photocoagulation apparatus 1.

The optical fiber 61 guides light (i.e., aiming light, treatment light) output from the laser unit 2. The collimator lens unit 62 converts the light guided by the optical fiber 61 into a parallel light beam.

The optical scanner 63 deflects, in a two dimensional manner, the light that has been converted into the parallel light beam by the collimator lens unit 62. The optical scanner 63 includes, for example, a single two dimensional optical scanner or two pieces of one dimensional optical scanners. The optical scanner 63 includes an optical scanner of any kind such as a galvano scanner and a MEMS optical scanner. The optical scanner 63 operates under the control of the laser controller 211.

The deflection member 64 is arranged behind the objective lens 21 and deflects the light that has passed through the optical scanner 63 to direct the light to the patient's eye E through the objective lens 21.

Note that a group of elements arranged in the optical path between the laser unit 2 and the objective lens 21 is not limited to the present example.

As described above, the photocoagulation apparatus 1B according to the present modification example is used to apply subthreshold coagulation to the retina Er of the patient's eye E, and includes the light guiding system (the optical fiber 61, the collimator lens unit 62, the optical scanner 63, and the deflection member 64), the photography system 30, the image detecting processor 232, the OCT system 40, the movement controller 212, the first memory (the memory 220), the scan controller 213, the image constructing processor (the OCT image constructing processor 231), the change information acquiring processor 233, and the display controller 214.

The light guiding system is configured to guide the aiming light and the treatment light generated by the laser unit 2 to the retina Er.

The photography system 30 is configured to perform moving image photography of the retina Er at least while (at least during a period when) the light guiding system is guiding the aiming light.

The image detecting processor 232 is configured to repeat the detection of an image of the aiming light from a moving image acquired by the moving image photography.

OCT system 40 is configured to apply an OCT scan to the retina Er.

The movement controller 212 is configured to move a scan target area so that the scan target area includes an application position of the aiming light on the retina Er, by sequentially controlling the OCT system 40 based on the image of the aiming light sequentially detected by the image detecting processor 232.

The first memory is configured to store the first OCT image of the retina Er (the reference OCT image) in advance.

The scan controller 213 is configured to control the OCT system 40, after the light guiding system guides the treatment light in response to a reception of an instruction from the user, to apply an OCT scan to the scan target area at a time of the reception of the instruction.

The image constructing processor is configured to construct the second OCT image from data acquired by the OCT scan applied to the retina Ef after the application of the treatment light.

The change information acquiring processor 233 is configured to acquire change information representing a tissue change in the retina Er caused by the treatment light, by comparing the first OCT image and the second OCT image with each other.

The display controller 214 is configured to display a change image based on the change information on a display device 300 together with a retinal image.

According to the photocoagulation apparatus 1B as described above, the state of tissue changes caused by the treatment light can be visualized in real time by performing an OCT scan after the application of the treatment light for subthreshold coagulation while moving the target area of the OCT scan in accordance with the movement of the image of the aiming light formed on the retina Er. In other words, the photocoagulation apparatus 1B is capable of visualizing in real time and appropriately presenting to the user, the state of tissue changes in a deep part of the retina that occur in the subthreshold coagulation treatment.

Any of the configurations and/or any of the functions of the photocoagulation apparatus 1 according to the above embodiment example may be combined with the photocoagulation apparatus 1B according to the present modification example. Further, any of the configurations and/or any of the functions of the photocoagulation apparatus 1A according to the above modification example may be combined with the photocoagulation apparatus 1B according to the present modification example. In addition, any known method or technique may be combined with the photocoagulation apparatus 1B according to the present modification example.

<Eye Fundus Observation Apparatus>

An eye fundus observation apparatus according to an embodiment example will be described. The eye fundus observation apparatus according to the present embodiment example is used together with a photocoagulation apparatus configured to apply subthreshold coagulation to a retina.

Figure 10:
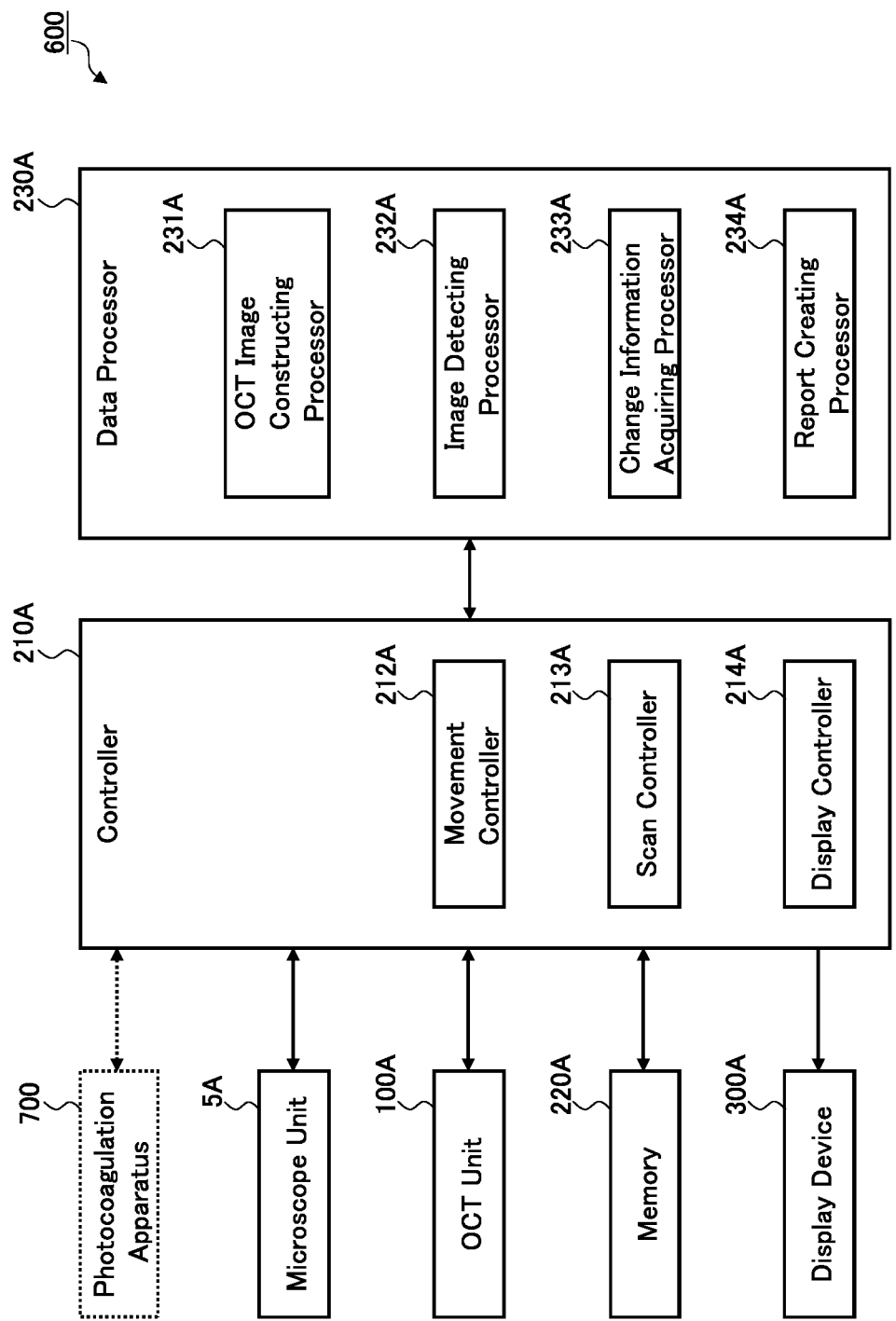
FIG. 10 is a schematic diagram illustrating the configuration of the eye fundus observation apparatus according to the embodiment example.

FIG. 10 shows the configuration of the eye fundus observation apparatus according to the present embodiment example. The eye fundus observation apparatus 600 includes the microscope unit 5A, the OCT unit 100A, the controller 210A, and the data processor 230A. The display device 300A may be an element of the eye fundus observation apparatus 600, or may be a peripheral device connected to the eye fundus observation apparatus 600.

The microscope unit 5A may have the same or similar configuration as or to the microscope unit 5 of the photocoagulation apparatus 1 according to the above embodiment example, and have the same or similar functions as or to the microscope unit 5.

The OCT unit 100A may have the same or similar configuration as or to the OCT unit 100 of the photocoagulation apparatus 1 according to the above embodiment example, and have the same or similar functions as or to the OCT unit 100.

The controller 210A may have the same or similar configuration as or to the controller 210 of the photocoagulation apparatus 1 according to the above embodiment example, and have the same or similar functions as or to the controller 210. However, the controller 210A is not required to have a configuration and a function corresponding to the laser controller 211 of the controller 210. An element corresponding to the laser controller 211 is provided in the photocoagulation apparatus 700 used together with the eye fundus observation apparatus 600. The controller 210A includes the movement controller 212A, the scan controller 213A, and the display controller 214A.

The movement controller 212A may have the same or similar configuration as or to the movement controller 212 according to the above embodiment example, and have the same or similar functions as or to the movement controller 212. The scan controller 213A may have the same or similar configuration as or to the scan controller 213 according to the above embodiment example, and have the same or similar functions as or to the scan controller 213. The display controller 214A may have the same or similar configuration as or to the display controller 214 according to the above embodiment example, and have the same or similar functions as or to the display controller 214.

The data processor 230A may have the same or similar configuration as or to the data processor 230 of the photocoagulation apparatus 1 according to the above embodiment example, and have the same or similar functions as or to the data processor 230. The data processor 230A includes the OCT image constructing processor 231A, the image detecting processor 232A, the change information acquiring processor 233A, and the report creating processor 234A.

The OCT image constructing processor 231A may have the same or similar configuration as or to the OCT image constructing processor 231 according to the above embodiment example, and have the same or similar functions as or to the OCT image constructing processor 231. The image detecting processor 232A may have the same or similar configuration as or to the image detecting processor 232 according to the above embodiment example, and have the same or similar functions as or to the image detecting processor 232. The change information acquiring processor 233A may have the same or similar configuration as or to the change information acquiring processor 233 according to the above embodiment example, and have the same or similar functions as or to the change information acquiring processor 233. The report creating processor 234A may have the same or similar configuration as or to the report creating processor 234 according to the above embodiment example, and have the same or similar functions as or to the report creating processor 234.

According to the eye fundus observation apparatus 600 configured in this way, the state of tissue changes caused by the treatment light can be visualized in real time by performing an OCT scan after the application of the treatment light for subthreshold coagulation carried out by using the photocoagulation apparatus 700 while moving the target area of the OCT scan in accordance with the movement of the image of the aiming light formed on the retina Er by the photocoagulation apparatus 700. In other words, the eye fundus observation apparatus 600 is capable of visualizing in real time and appropriately presenting to the user, the state of tissue changes in a deep part of the retina that occur in the subthreshold coagulation treatment.

Any of the configurations and/or any of the functions of the photocoagulation apparatus 1 according to the above embodiment example may be combined with the eye fundus observation apparatus 600 according to the present embodiment example. Further, any of the configurations and/or any of the functions of the photocoagulation apparatus 1A according to the above modification example may be combined with the eye fundus observation apparatus 600 according to the present embodiment example. Furthermore, any of the configurations and/or any of the functions of the photocoagulation apparatus 1B according to the above modification example may be combined with the eye fundus observation apparatus 600 according to the present embodiment example. In addition, any known method or technique may be combined with the eye fundus observation apparatus 600 according to the present embodiment example.

<Control Method, Program, Recording Medium>

A description will be given of a control method, a program, and a recording medium according to some embodiment examples.

A control method corresponding to the above photocoagulation apparatus 1 will be described. The control method is a method of controlling a photocoagulation apparatus (1). The photocoagulation apparatus (1) includes a light guiding system (the optical fiber 3 and the probe 4) and an OCT system (40), and is used to apply subthreshold coagulation to a retina (Er) via a probe (4). The light guiding system is configured to guide aiming light and treatment light to the retina (Er) via the probe (4) inserted in the patient's eye (E), and the OCT system (40) is configured to apply an OCT scan to the retina (Er).

The control method of the photocoagulation apparatus (1) includes a first memory step, a photography step, an image detecting step, an OCT step, a movement control step, a scan control step, an image constructing step, a change information acquiring step, and a display control step.

The first memory step stores the first OCT image (the reference OCT image) of the retina (Er) in advance.

The photography step performs moving image photography of the retina (Er) at least while (at least during a period when) the light guiding system is guiding the aiming light.

The image detecting step repeatedly detects an image of the aiming light from a moving image acquired by the moving image photography.

The OCT step applies an OCT scan to the retina (Er) by the OCT system (40).

The movement control step moves a scan target area to include an application position of the aiming light on the retina (Er) by sequentially controlling the OCT system (40) based on the image of the aiming light sequentially detected by the image detecting step.

The scan control step controls the OCT system (40), after the light guiding system guides the treatment light upon receiving an instruction from a user, to apply an OCT scan to the scan target area at a time of reception of the instruction.

The image constructing step constructs the second OCT image from data acquired by the OCT scan.

The change information acquiring step acquires change information representing a tissue change in the retina (Er) caused by the treatment light by comparing the first OCT image and the second OCT image with each other.

The display control step displays a change image based on the change information on a display device (300) together with a retinal image.

According to the control method of the photocoagulation apparatus (1) as described above, the state of tissue changes caused by the treatment light can be visualized in real time by performing an OCT scan after the application of the treatment light for subthreshold coagulation while moving the target area of the OCT scan in accordance with the movement of the image of the aiming light formed on the retina (Er). In other words, the control method makes it possible to visualize in real time and appropriately present to the user, the state of tissue changes in a deep part of the retina that occur in the subthreshold coagulation treatment. Subthreshold coagulation can also be properly performed in the case of using the probe (4) inserted into the eye.

Any of the functions, any of the processing, any of the processes, any of the operations, etc. described in any of the above-described embodiment examples can be combined with the control method according to the present embodiment example.

It is possible to configure a program that causes a computer (200) to execute the control method of the photocoagulation apparatus (1) according to the present embodiment example. In addition, it is possible to create a computer-readable non-transitory recording medium that stores the program configured in this way. The non-transitory recording medium may be in any form, and examples thereof include a magnetic disk, an optical disk, a magneto-optical disk, a semiconductor memory, and the like.

Next, a control method corresponding to the above photocoagulation apparatus 1B will be described. The control method is a method of controlling a photocoagulation apparatus (1B). A photocoagulation apparatus (1B) includes a light guiding system (the optical fiber 61, the collimator lens unit 62, the optical scanner 63, and the deflection member 64) and an OCT system (40), and is used to apply subthreshold coagulation to a retina (Er). The light guiding system is configured to guide aiming light and treatment light to the retina of the patient's eye, and the OCT system (40) is configured to apply an OCT scan to the retina (Er).

The control method of the photocoagulation apparatus (1B) includes a first memory step, a photography step, an image detecting step, an OCT step, a movement control step, a scan control step, an image constructing step, a change information acquiring step, and a display control step.

The first memory step stores the first OCT image (the reference OCT image) of the retina (Er) in advance.

The photography step performs moving image photography of the retina (Er) at least while (at least during a period when) the light guiding system is guiding the aiming light.

The image detecting step repeatedly detects an image of the aiming light from a moving image acquired by the moving image photography.

The OCT step applies an OCT scan to the retina (Er) by the OCT system (40).

The movement control step moves a scan target area to include an application position of the aiming light on the retina (Er) by sequentially controlling the OCT system (40) based on the image of the aiming light sequentially detected by the image detecting step.

The scan control step controls the OCT system (40), after the light guiding system guides the treatment light upon receiving an instruction from a user, to apply an OCT scan to the scan target area at a time of reception of the instruction.

The image constructing step constructs the second OCT image from data acquired by the OCT scan.

The change information acquiring step acquires change information representing a tissue change in the retina (Er) caused by the treatment light by comparing the first OCT image and the second OCT image with each other.

The display control step displays a change image based on the change information on a display device (300) together with a retinal image.

According to the control method of the photocoagulation apparatus (1B) as described above, the state of tissue changes caused by the treatment light can be visualized in real time by performing an OCT scan after the application of the treatment light for subthreshold coagulation while moving the target area of the OCT scan in accordance with the movement of the image of the aiming light formed on the retina (Er). In other words, the control method makes it possible to visualize in real time and appropriately present to the user, the state of tissue changes in a deep part of the retina that occur in the subthreshold coagulation treatment.

Any of the functions, any of the processing, any of the processes, any of the operations, etc. described in any of the above-described embodiment examples can be combined with the control method according to the present embodiment example.

It is possible to configure a program that causes a computer (200) to execute the control method of the photocoagulation apparatus (1B) according to the present embodiment example. In addition, it is possible to create a computer-readable non-transitory recording medium that stores the program configured in this way. The non-transitory recording medium may be in any form, and examples thereof include a magnetic disk, an optical disk, a magneto-optical disk, a semiconductor memory, and the like.

Next, a control method corresponding to the above eye fundus observation apparatus 600 will be described. The control method is a method of controlling an eye fundus observation apparatus (600). An eye fundus observation apparatus (600) includes an OCT system (the OCT system 40; the microscope unit 5A, the OCT unit 100A) configured to apply an OCT scan to a retina (Er) of a patient's eye (E). The eye fundus observation apparatus (600) is used for applying subthreshold coagulation to the retina (Er) by a photocoagulation apparatus (700).

The control method of the eye fundus observation apparatus (600) includes a first memory step, a photography step, an image detecting step, an OCT step, a movement control step, a scan control step, an image constructing step, a change information acquiring step, and a display control step.

The first memory step stores the first OCT image (the reference OCT image) of the retina (Er) in advance.

The photography step performs moving image photography of the retina (Er) at least while (at least during a period when) the light guiding system is guiding the aiming light.

The image detecting step repeatedly detects an image of the aiming light from a moving image acquired by the moving image photography.

The OCT step applies an OCT scan to the retina (Er) by the OCT system (the OCT system 40; the microscope unit 5A, the OCT unit 100A).

The movement control step moves a scan target area to include an application position of the aiming light on the retina (Er) by sequentially controlling the OCT system (the OCT system 40; the microscope unit 5A, the OCT unit 100A) based on the image of the aiming light sequentially detected by the image detecting step.

The scan control step controls the OCT system (the OCT system 40; the microscope unit 5A, the OCT unit 100A), after the photocoagulation apparatus (700) guides the treatment light upon receiving an instruction from a user, to apply an OCT scan to the scan target area at a time of reception of the instruction.

The image constructing step constructs the second OCT image from data acquired by the OCT scan.

The change information acquiring step acquires change information representing a tissue change in the retina (Er) caused by the treatment light by comparing the first OCT image and the second OCT image with each other.

The display control step displays a change image based on the change information on a display device (300A) together with a retinal image.

According to the control method of the eye fundus observation apparatus (600) as described above, the state of tissue changes caused by the treatment light can be visualized in real time by performing an OCT scan after the application of the treatment light for subthreshold coagulation performed by the photocoagulation apparatus (700) while moving the target area of the OCT scan in accordance with the movement of the image of the aiming light formed on the retina (Er) by the photocoagulation apparatus (700). In other words, the control method makes it possible to visualize in real time and appropriately present to the user, the state of tissue changes in a deep part of the retina that occur in the subthreshold coagulation treatment.

Any of the functions, any of the processing, any of the processes, any of the operations, etc. described in any of the above-described embodiment examples can be combined with the control method according to the present embodiment example.

It is possible to configure a program that causes a computer (200A) to execute the control method of the eye fundus observation apparatus (600) according to the present embodiment example. Also, it is possible to create a computer-readable non-transitory recording medium that stores the program configured in this way. The non-transitory recording medium may be in any form, and examples thereof include a magnetic disk, an optical disk, a magneto-optical disk, a semiconductor memory, and the like.

The embodiment examples described above are merely typical examples of the present disclosure. Therefore, any modification (omission, substitution, replacement, addition, etc.) within the scope of the gist of the present disclosure may be appropriately applied.

While certain embodiments have been described, these embodiments have been presented by way of example only, and are not intended to limit the scope of the inventions. Indeed, the novel embodiments described herein may be embodied in a variety of other forms; furthermore, various omissions, substitutions, additions and changes in the form of the embodiments described herein may be made without departing from the spirit of the inventions. The accompanying claims and their equivalents are intended to cover such forms or modifications as would fall within the scope and spirit of the inventions.

What is claimed is:

1. A photocoagulation apparatus for applying subthreshold coagulation to a retina via a probe inserted into an eye, comprising:
    a light guiding system configured to guide aiming light and treatment light to the retina via the probe;
    a photography system configured to perform moving image photography of the retina to obtain a moving image of the retina viewed from a front of the eye at least while the light guiding system is guiding the aiming light before guiding the treatment light;
    an image detecting processor configured to repeatedly detect an image of the aiming light formed on a surface of the retina from the moving image acquired by the moving image photography;
    an optical coherence tomography (OCT) system configured to apply an OCT scan to the retina;
    a movement controller configured to move a scan target area to include an application position of the aiming light on the surface of the retina by sequentially controlling the OCT system based on the image sequentially detected by the image detecting processor;
    a first memory configured to store a first OCT image of the retina in advance;
    a scan controller configured to control the OCT system, after the light guiding system guides the treatment light upon receiving an instruction from a user, to apply an OCT scan to the scan target area at a time of reception of the instruction;
    an image constructing processor configured to construct a second OCT image from data acquired by the OCT scan;
    a change information acquiring processor configured to acquire change information representing a tissue change in the retina caused by the treatment light by comparing the first OCT image and the second OCT image with each other; and
    a display controller configured to display a change image based on the change information on a display device together with a retinal image viewed from the front of the eye.

2. The photocoagulation apparatus of claim 1, wherein
    the scan controller controls the OCT system to perform an OCT scan each time the light guiding system guides the treatment light,
    the image constructing processor constructs a second OCT image each time an OCT scan is performed by the OCT system,
    the change information acquiring processor acquires change information each time a second OCT image is constructed by the image constructing processor, and
    the display controller updates a display of a change image presented to the user together with the retinal image each time change information is acquired by the change information acquiring processor.

3. The photocoagulation apparatus of claim 2, wherein the scan controller controls the OCT system to perform an OCT scan immediately after the light guiding system guides the treatment light.

4. The photocoagulation apparatus of claim 1, wherein
    the scan controller controls the OCT system, after the treatment light is applied to each of a plurality of positions on the retina, to apply an OCT scan to an area that includes all of the plurality of positions,
    the image constructing processor constructs a third OCT image from data acquired by the OCT scan applied to the area,
    the change information acquiring processor acquires first change distribution information representing a distribution of tissue changes in the retina in the area by comparing the first OCT image and the third OCT image with each other, and
    the display controller controls the display device to display a first change distribution image based on the first change distribution information together with a retinal image.

5. The photocoagulation apparatus of claim 4, wherein each of a plurality of scan target areas respectively corresponding to the plurality of positions is smaller than the area that includes all of the plurality of positions.

6. The photocoagulation apparatus of claim 4, wherein
    the change information acquiring processor acquires second change distribution information representing a distribution of tissue changes in the retina in the area that includes all of the plurality of positions by comparing the second OCT image and the third OCT image with each other, and
    the display controller controls the display device to display a second change distribution image based on the second change distribution information together with a retinal image.

7. The photocoagulation apparatus of claim 1, wherein
    the change information acquiring processor constructs motion contrast data from two or more OCT images acquired from substantially a same position of the retina at different times, and determines a tissue change in the retina from the motion contrast data.

8. The photocoagulation apparatus of claim 1, wherein
    the display controller displays the retinal image on a first layer, and displays, on a second layer overlaid on the first layer, an image based on information acquired by the change information acquiring processor.

9. The photocoagulation apparatus of claim 8, wherein the display controller displays an application condition of the treatment light guided by the light guiding system together with the image based on the information acquired by the change information acquiring processor.

10. The photocoagulation apparatus of claim 1, further comprising:
    a second memory configured to store a template of a treatment report in advance; and
    a report creating processor configured to enter data in the template based at least on the information acquired by the change information acquiring processor.

11. The photocoagulation apparatus of claim 1, wherein the retinal image is any of an image of the retina acquired by a fundus camera, an image of the retina acquired by a scanning laser ophthalmoscope, an image of the retina acquired by a surgical microscope, an image of the retina acquired by a slit lamp microscope, and a front image of the retina acquired by using OCT.

12. The photocoagulation apparatus of claim 1, further comprising:
    an observation system configured for the user to observe a magnified image of the retina via an eyepiece; and
    an optical path coupling member configured to couple an optical path starting from the display device with an optical path of the observation system toward the eyepiece.

13. A method of controlling a photocoagulation apparatus that applies subthreshold coagulation to a retina via a probe inserted into a patient's eye and includes a light guiding system configured to guide aiming light and treatment light to the retina via the probe and an optical coherence tomography (OCT) system configured to apply an OCT scan to the retina, the method comprising:
- a first memory step of storing a first OCT image of the retina;
- a photography step of performing moving image photography of the retina to obtain a moving image of the retinal viewed from a front of the eye at least while the light guiding system is guiding the aiming light before guiding the treatment light;
- an image detecting step of repeatedly detecting an image of the aiming light formed on a surface of the retina from the moving image acquired by the moving image photography;
- an OCT step of applying an OCT scan to the retina by the OCT system;
- a movement control step of moving a scan target area to include an application position of the aiming light on the surface of the retina by sequentially controlling the OCT system based on the image sequentially detected by the image detecting step;
- a scan control step of controlling the OCT system, after the light guiding system guides the treatment light upon receiving an instruction from a user, to apply an OCT scan to the scan target area at a time of reception of the instruction;
- an image constructing step of constructing a second OCT image from data acquired by the OCT scan;
- a change information acquiring step of acquiring change information representing a tissue change in the retina caused by the treatment light by comparing the first OCT image and the second OCT image with each other; and
- a display control step of displaying a change image based on the change information on a display device together with a retinal image viewed from the front of the eye.

14. A computer-readable non-transitory recording medium storing a program causing a computer to execute the method of claim 13.

* * * * *